(12) United States Patent
Laird et al.

(10) Patent No.: US 9,765,379 B2
(45) Date of Patent: Sep. 19, 2017

(54) HARVEST OPERATIONS FOR RECOMBINANT PROTEINS

(71) Applicant: Genentech, Inc., South San Francisco, CA (US)

(72) Inventors: Michael W. Laird, San Ramon, CA (US); Richard St. John, Millbrae, CA (US); Jane V. Gunson, Redwood City, CA (US); Kimberly Kaleas, San Mateo, CA (US); Deepa Nadarajah, San Mateo, CA (US); Rachel L E Adams, Guelph (CA); Bradley R. Snedecor, Portola Valley, CA (US)

(73) Assignee: Genentech, Inc., South San Francisco, CA (US)

(*) Notice: Subject to any disclaimer, the term of this patent is extended or adjusted under 35 U.S.C. 154(b) by 361 days.

(21) Appl. No.: 14/497,964

(22) Filed: Sep. 26, 2014

(65) Prior Publication Data

US 2015/0225760 A1    Aug. 13, 2015

Related U.S. Application Data

(63) Continuation of application No. PCT/US2013/031383, filed on Mar. 14, 2013.

(60) Provisional application No. 61/616,297, filed on Mar. 27, 2012.

(51) Int. Cl.
*C12P 21/00* (2006.01)
*C07K 16/00* (2006.01)

(52) U.S. Cl.
CPC .............. *C12P 21/00* (2013.01); *C07K 16/00* (2013.01)

(58) Field of Classification Search
None
See application file for complete search history.

(56) References Cited

U.S. PATENT DOCUMENTS

2009/0053786 A1    2/2009    Kao et al.

FOREIGN PATENT DOCUMENTS

| CN | 101932591 A | 12/2010 |
|---|---|---|
| EP | 1607383 | 12/2005 |
| JP | 2007-501623 A | 2/2007 |
| JP | 2008-011854 A | 1/2008 |
| JP | 2009-536033 A | 10/2009 |
| JP | 2010-088387 A | 2/2010 |

OTHER PUBLICATIONS

Johnson et al. (The menD and menE homologs code for 2-succinyl-6-hydroxyl-2, 4-cyclohexadiene-1-carboxylate synthase and O-succinylbenzoic acid—CoA synthase in the phylloquinone biosynthetic pathway of *Synechocystis* sp. PCC 6803, Biochimica et Biophysica Acta, 1557 (2003), 67-76).*

Chen, X, et al., "Improved glucosamine and N-acetylglucosamine production by an engineered *Escherichia coli* via step-wise regulation of dissolved oxygen level"Bioresource Technology 110:534-538 (Dec. 11, 2011).

Furuichi, K. et al., "Optimal aerobic cultivation method for 1,4-dihydroxy-2-naphthoic acid production by Propionibacterium freudenreichii ET-3" Journal of Bioscience and Bioengineering 102:198-205 (2006).

International Search Report of PCT/US2013/031383, in 4 pages (Mailed: Jun. 18, 2013).

Nadarajah, D. et al, "Manufacturing-Scale Implentation of Enhanced Harvest Process Controls to Inhibit Colored Protein-Adduct Formation in Prokaryotic Host Cell Derived Recombinant Protein", AIChe 2012 Annual Meeting; retrieved from the internet: URL:http://www3.aiche.org/Proceedings/Abstract.aspx/PaperID=274973, in 1 page (Oct. 2012).

Pizarro, S. et al., "High-yield expression of human vascular endothelial growth factor VEGF165 in *Escherichia coli* and purification for therapeutic applications" Protein Expression and Purification 72:184-193 (2010).

Rao, D. et al., "Impact of dissolved oxygen concentration on some key parameters and production of rhG-CSF in batch fermentation" Journal of Industrial Microbiology and Biotechnology 35:991-1000 (2008).

Shaw, D. et al., "Characterization of *Escherichia coli* men mutants defective in conversion of o-succinylbenzoate to 1,4-dihydroxy-2-naphthoate" Journal of Bacteriology 152:1132-1137 (1982).

Written Opinion issued in Singapore Patent Application No. 1120146112T, dated May 5, 2015 (in 8 pages).

* cited by examiner

*Primary Examiner* — Suzanne M Noakes
*Assistant Examiner* — Jae W Lee
(74) *Attorney, Agent, or Firm* — James E. Nesbitt

(57) ABSTRACT

The present invention contemplates methods of producing a recombinant protein comprising fermenting a prokaryotic host cell wherein said prokaryotic host cell has been transformed with a nucleic acid encoding said recombinant protein, harvesting said recombinant protein under conditions where $dO_2$ levels are greater than 0%, purifying said recombinant protein to a filtered bulk, wherein said filtered bulk does not contain detectable DHNA-recombinant protein adduct, as measured by an IEC assay at 310 nm. Furthermore, method of producing a recombinant protein comprising fermenting a menE gene-deleted prokaryotic host cell wherein said prokaryotic host cell has been transformed with a nucleic acid encoding said recombinant protein, harvesting said recombinant protein, purifying said recombinant protein to a filtered bulk, wherein said filtered bulk does not contain detectable DHNA-recombinant protein adduct, as measured by an IEC assay at 310 nm, wherein the recombinant protein yield is increased by about 20% or greater is contemplated.

4 Claims, 12 Drawing Sheets

PW = Purified Water
C = Development Control Run
1 = Run 1
2 = Run 2
3 = Run 3

HARVEST OPERATIONS FOR RECOMBINANT PROTEINS

CROSS REFERENCE TO RELATED APPLICATIONS

This application is a continuation of International Patent Application No. PCT/US2013/031383, filed on Mar. 14, 2013, which claims the benefit of priority of provisional U.S. Application No. 61/616,297, filed on Mar. 27, 2012, the entire contents of which are incorporated herein by reference.

FIELD OF THE INVENTION

The invention relates to improved methods for culturing recombinant proteins in prokaryotic host cells.

BACKGROUND OF THE INVENTION

The large-scale, economic purification of proteins is required for viable biotechnology products. Generally, proteins are produced by cell culture, using either mammalian or bacterial cell lines engineered to produce the protein of interest by insertion of a recombinant plasmid containing the gene for that protein. Since the cell lines used are living organisms, they must be fed with a complex growth medium which usually contains a mixture of salts, sugars, amino acids, vitamins, trace elements and peptones. Separation of the desired protein from the mixture of compounds fed to the cells and from the by-products of the cells themselves to a purity sufficient for use as a human therapeutic poses a formidable challenge.

Recombinant therapeutic proteins are commonly produced in several host cell lines including mammalian host cells, such as, for example, murine myeloma NS0 and Chinese Hamster Ovary (CHO) cells (Anderson, D. C and Krummen, L. (2002) Curr. Opin. Biotech. 13: 117-123; Chu, L. and Robinson, D. K. (2001) Curr. Opin. Biotechnol. 12:180-187) and bacterial host cells including *Escherichia coli* (*E. coli*). Each cell line has advantages and disadvantages in terms of productivity and the characteristics of the proteins produced by the cells. *Escherichia coli* has been most extensively used for the large-scale production of therapeutic proteins, which do not require complex glycosylation for bioactivity. Heterologous proteins expressed by *E. coli* may accumulate as soluble product or insoluble aggregates. Generally, to isolate the proteins, the cells may be subjected to treatments for periplasmic extraction or be lysed to release intracellular products that are otherwise inaccessible. Advances in fermentation and cell culture techniques have greatly increased the titers of targeted recombinant proteins.

Choices of commercial production cell lines often balance the need for high productivity with the ability to deliver the product quality attributes required of a given product. Under cGMP fermentation procedures, quality is built into the entire process ensuring that regulatory agencies requirements are met in terms of safety, product identity, quality and purity. However, occasionally issues arise in which a given product does not meet its specifications. The challenge is to develop a robust process in which to identify and isolate the issue, then mitigate the issue such that process controls can be maintained within established parameter ranges, and make sure the process consistently produces a product that meets product specifications. There is a need in the art for mitigating or eliminating the incidence of products that do not meet specifications.

SUMMARY OF THE INVENTION

The present invention contemplates a method of producing a recombinant protein comprising (a) fermenting a prokaryotic host cell wherein said prokaryotic host cell has been transformed with a nucleic acid encoding said recombinant protein, and (b) harvesting said recombinant protein under conditions where dissolved oxygen ($dO_2$) levels are greater than 0%, and (c) purifying said recombinant protein to a filtered bulk for storage (FBS), wherein said filtered bulk does not contain detectable 1,4-dihydroxy-2-naphthoate (DHNA)-recombinant protein adduct, as measured by an ion exchange chromatography (IEC) assay at 310 nm. In one embodiment, in the method described above, the analytical assay is by HPLC, RP HPLC, HIC HPLC, NMR, mass spectrometry, or UV spectroscopy.

The present invention contemplates a method of producing a recombinant protein comprising (a) fermenting a prokaryotic host cell wherein said prokaryotic host cell has been transformed with a nucleic acid encoding said recombinant protein, and (b) harvesting said recombinant protein under conditions where $dO_2$ levels are greater than 0%, and (c) purifying said recombinant protein to a FBS, wherein said filtered bulk does not contain detectable DHNA-recombinant protein adduct, as measured by an IEC assay at 310 nm, wherein said recombinant protein is a recombinant polypeptide or an isolated antibody.

The present invention contemplates a method of producing a recombinant protein comprising (a) fermenting a prokaryotic host cell wherein said prokaryotic host cell has been transformed with a nucleic acid encoding said recombinant protein, and (b) harvesting said recombinant protein under conditions where $dO_2$ levels are greater than 0%, and (c) purifying said recombinant protein to a FBS, wherein said filtered bulk does not contain detectable DHNA-recombinant protein adduct, as measured by an IEC assay at 310 nm, wherein the fermentation is scale-independent.

The present invention contemplates a method of producing a recombinant protein comprising (a) fermenting a prokaryotic host cell wherein said prokaryotic host cell has been transformed with a nucleic acid encoding said recombinant protein, and (b) harvesting said recombinant protein under conditions where $dO_2$ levels are greater than 0%, and (c) purifying said recombinant protein to a FBS, wherein said filtered bulk does not contain detectable DHNA-recombinant protein adduct, as measured by an IEC assay at 310 nm, wherein said prokaryotic host cell is *Escherichia coli* (*E. coli*), *Enterobacter*, *Azotobacter*, *Erwinia*, *Bacillus*, *Pseudomonas*, *Klebsiella*, *Proteus*, *Salmonella*, *Serratia*, *Shigella*, *Rhizobia*, *Vitreoscilla*, and *Paracoccus*.

The present invention contemplates a method of producing a recombinant protein comprising (a) fermenting a prokaryotic host cell wherein said prokaryotic host cell has been transformed with a nucleic acid encoding said recombinant protein, and (b) harvesting said recombinant protein under conditions where $dO_2$ levels are greater than 0%, and (c) purifying said recombinant protein to a FBS, wherein said filtered bulk does not contain detectable DHNA-recombinant protein adduct, as measured by an IEC assay at 310 nm, wherein said $dO_2$ is maintained at levels greater than 0% continuously throughout the harvest operations of step (b). In one embodiment in the method described above, the harvest operations comprise a homogenization stage. In another embodiment, the dO$_2$ is maintained at about 30% to about 75% prior to homogenization. In yet another embodiment, the dO$_2$ is maintained at levels greater than 75% prior to homogenization. In still another embodiment, the dO$_2$ is maintained at about 50% after homogenization. In another embodiment, the dO$_2$ is maintained at levels greater than 50% after homogenization. In one embodiment, the dO$_2$ is maintained for a period of greater than or equal to 1.5 hours. In still another embodiment, the dO$_2$ is maintained for a period of greater than or equal to 2 hours.

The present invention contemplates a method of producing a recombinant protein comprising (a) fermenting a prokaryotic host cell wherein said prokaryotic host cell has been transformed with a nucleic acid encoding said recombinant protein, and (b) harvesting said recombinant protein under conditions where dO$_2$ levels are greater than 0%, and (c) purifying said recombinant protein to a FBS, wherein said filtered bulk does not contain detectable DHNA-recombinant protein adduct, as measured by an IEC assay at 310 nm, wherein the dO$_2$ is maintained with overlay or sparged air, with increased back-pressure, or with agitation (i.e. stirring). In one embodiment, the overlay air is from about 0.4 vvm to about 0.8 vvm. In another embodiment, the overlay air is targeted at 0.6 vvm. In another embodiment, the increased backpressure is between about 1.0 to about 30 psi. In one embodiment, the increased backpressure is targeted at 19 psi. In still another embodiment, the agitation rate is from about 6 Watts/L to about 8 Watts/L. In yet another embodiment, the agitation rate is at least 6 Watts/L. In another embodiment, the agitation rate is targeted at 6 Watts/L.

In another aspect of the present invention, a method of producing a recombinant protein comprising (a) fermenting a menE gene-deleted prokaryotic host cell wherein said prokaryotic host cell has been transformed with a nucleic acid encoding said recombinant protein, (b) harvesting said recombinant protein; and (c) purifying said recombinant protein to a FBS, wherein said filtered bulk does not contain detectable DHNA-recombinant protein adduct, as measured by an IEC assay at 310 nm, is contemplated. As a further embodiment to the method described above, the recombinant protein yield is increased by about 20% or greater, by about 30% or greater, by about 40% or greater, by about 50% or greater, by about 60% or greater, as compared to the yield using a control prokaryotic host cell.

In another aspect of the present invention, a method of producing a recombinant protein comprising (a) fermenting a menE gene-deleted prokaryotic host cell wherein said prokaryotic host cell has been transformed with a nucleic acid encoding said recombinant protein, (b) harvesting said recombinant protein; and (c) purifying said recombinant protein to a FBS, wherein said filtered bulk does not contain detectable DHNA-recombinant protein adduct, as measured by an IEC assay at 310 nm, is contemplated, wherein the recombinant protein yield is increased by about 20% or greater, by about 30% or greater, by about 40% or greater, by about 50% or greater, by about 60% or greater, as compared to the yield using a control prokaryotic host cell, wherein the fermentation is scale-independent.

In another aspect of the present invention, a method of producing a recombinant protein comprising (a) fermenting a menE gene-deleted prokaryotic host cell wherein said prokaryotic host cell has been transformed with a nucleic acid encoding said recombinant protein, (b) harvesting said recombinant protein; and (c) purifying said recombinant protein to a FBS, wherein said filtered bulk does not contain detectable DHNA-recombinant protein adduct, as measured by an IEC assay at 310 nm, is contemplated, wherein the recombinant protein yield is increased by about 20% or greater, by about 30% or greater, by about 40% or greater, by about 50% or greater, by about 60% or greater, as compared to the yield using a control prokaryotic host cell, wherein said recombinant protein is a recombinant polypeptide or an isolated antibody.

In another aspect of the present invention, a method of producing a recombinant protein comprising (a) fermenting a menE gene-deleted prokaryotic host cell wherein said prokaryotic host cell has been transformed with a nucleic acid encoding said recombinant protein, (b) harvesting said recombinant protein; and (c) purifying said recombinant protein to a FBS, wherein said filtered bulk does not contain detectable DHNA-recombinant protein adduct, as measured by an IEC assay at 310 nm, is contemplated, wherein the recombinant protein yield is increased by about 20% or greater, by about 30% or greater, by about 40% or greater, by about 50% or greater, by about 60% or greater, as compared to the yield using a control prokaryotic host cell, wherein said prokaryotic host cell is *Escherichia coli* (*E. coli*), *Enterobacter*, *Azotobacter*, *Erwinia*, *Bacillus*, *Pseudomonas*, *Klebsiella*, *Proteus*, *Salmonella*, *Serratia*, *Shigella*, *Rhizobia*, *Vitreoscilla*, and *Paracoccus*.

Figure 9:
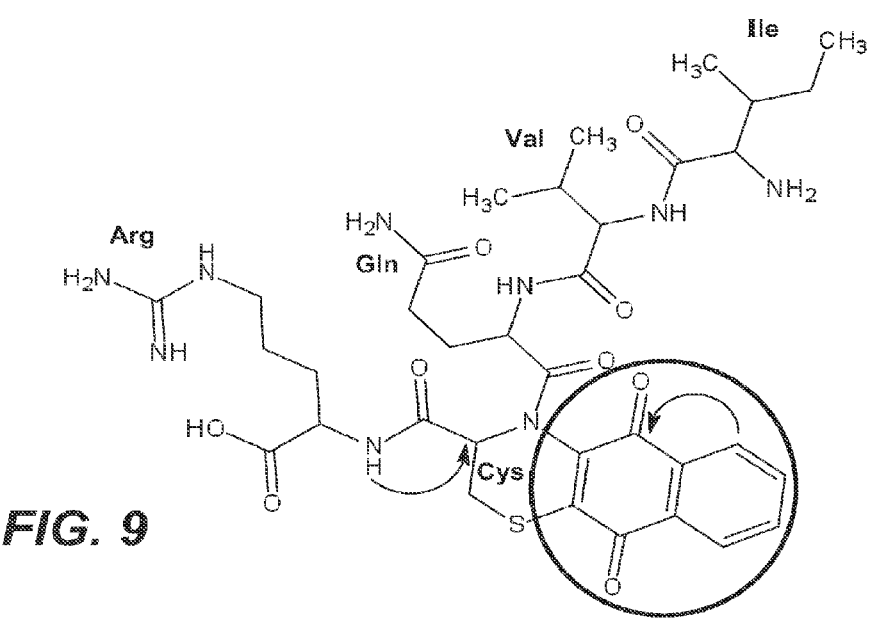

Based on the NMR data collected, the proposed structure of the brown adduct is presented in FIG. 9.

Figure 10:
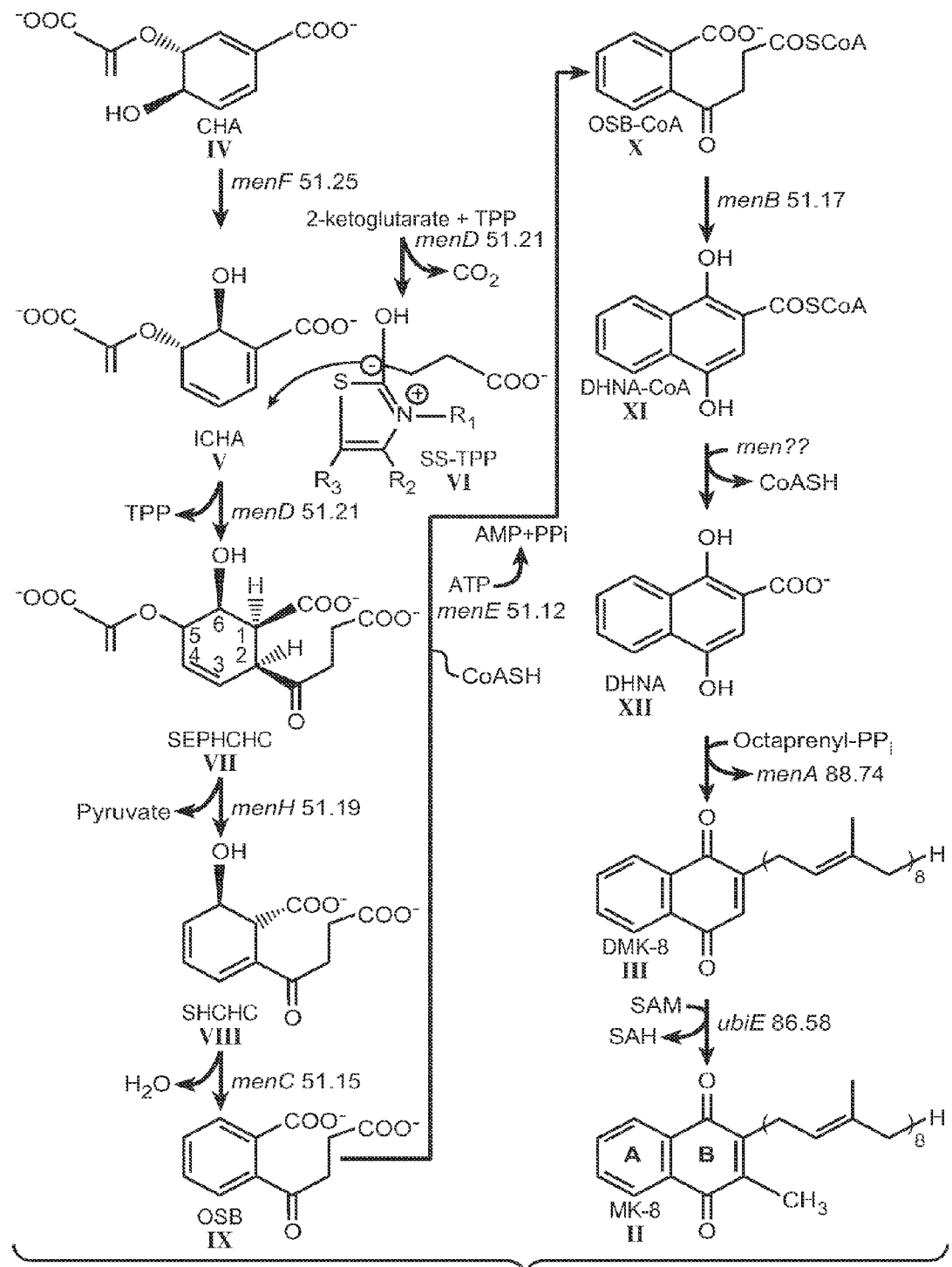

FIG. 10 shows the biosynthesis pathway in prokaryotic cells to make menaquinones.

Figure 11:
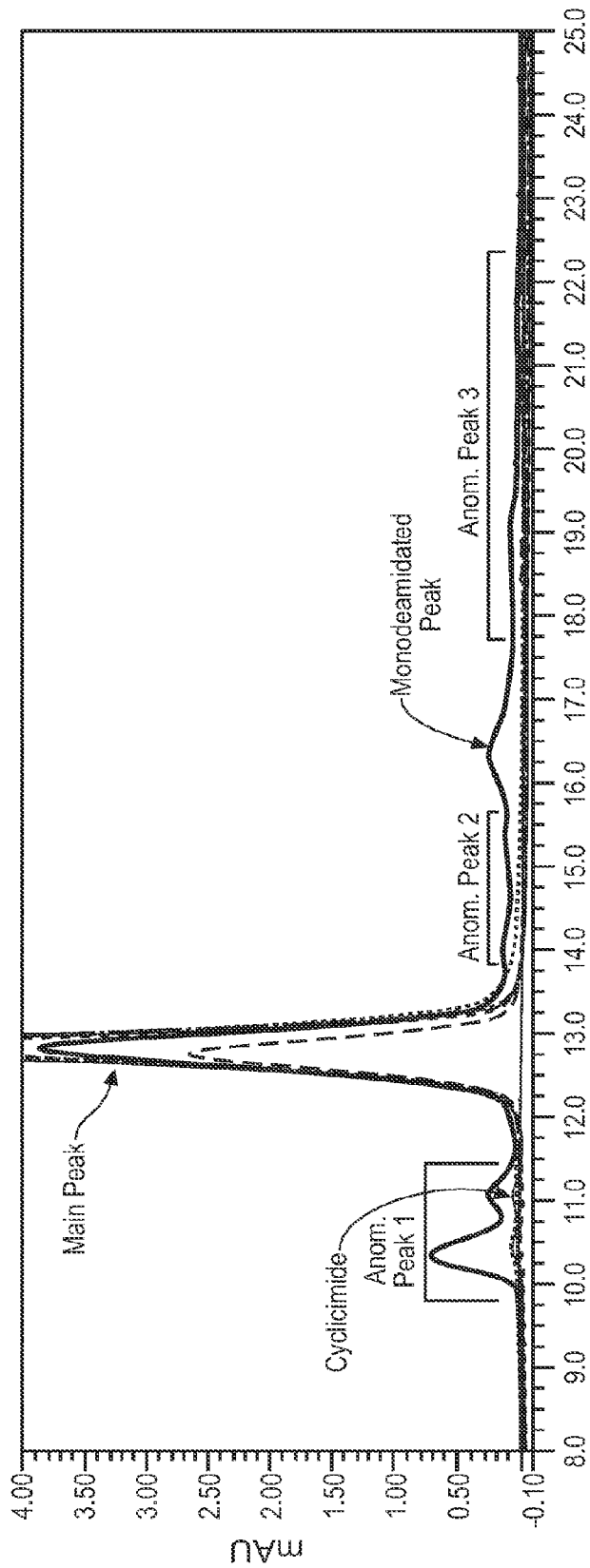

FIG. 11 shows a representative filtered bulk recombinant product tested for brown adduct formation by ion exchange chromatography at 310 nm and showed no measurable adduct formation.

Figure 12:
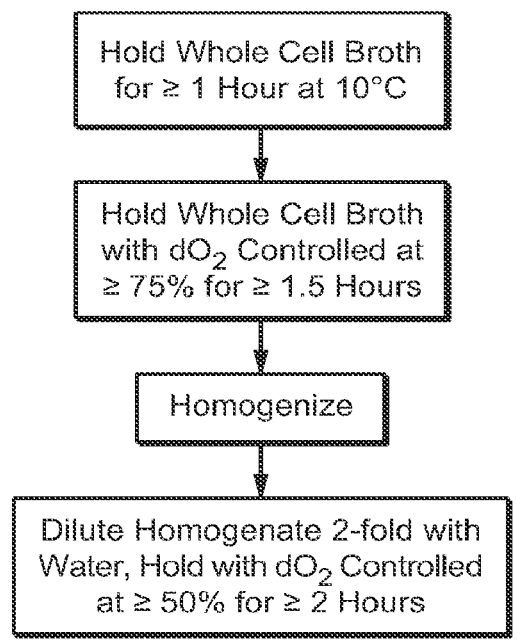

FIG. 12 shows an exemplary schematic of the Hi-dO process enhancements implemented around the harvest operations.

Figure 13:
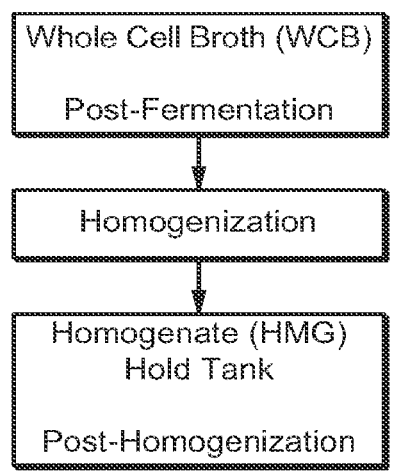

FIG. 13 shows a schematic that shows the three major stages of a typical harvest operation: post-fermentation stage, a homogenization stage, then a post-homogenization stage.

DETAILED DESCRIPTION OF EMBODIMENTS OF THE INVENTION

I. Definitions

Unless stated otherwise, the following terms and phrases as used herein are intended to have the following meanings:

The term "agitation rate" is mixing of the culture broth or of the homogenate, which is typically measured as revolutions per minute (rpm). In one embodiment, agitation rate can be measured by a "power per unit volume". For example, at 200 rpm in a 1,000 liter fermentor, the agitation rate has a value of approximately 6 Watts/L.

The term "antibody" herein is used in the broadest sense and specifically covers monoclonal antibodies, polyclonal antibodies, multispecific antibodies (e.g., bispecific antibodies), and antibody fragments, so long as they exhibit the desired biological activity. Antibodies may be murine, human, humanized, chimeric, or derived from other species. The term "antibody," as used herein, also refers to a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin disclosed herein can be of any type (e.g., IgG, IgE, IgM, IgD, and IgA), class (e.g., IgG1, IgG2, IgG3, IgG4, IgA1 and IgA2) or subclass of immunoglobulin molecule. The immunoglobulins can be derived from any species. In one aspect, however, the immunoglobulin is of human, murine, or rabbit origin.

"Antibody fragments" comprise a portion of a full length antibody, generally the antigen binding or variable region thereof. Examples of antibody fragments include Fab, Fab', F(ab')2, and Fv fragments; diabodies; linear antibodies; fragments produced by a Fab expression library, anti-idiotypic (anti-Id) antibodies, CDR (complementary determining region), ECD (extracellular domain), and epitope-binding fragments of any of the above which immunospecifically bind to cancer cell antigens, viral antigens or microbial antigens, single-chain antibody molecules; and multispecific antibodies formed from antibody fragments.

"Clarity, Opalescence and Coloration (COC) Assay" is defined as using identical test tubes of colourless, transparent, neutral glass with a flat base and an internal diameter of 15-25 mm, compare the liquid to be examined with a reference suspension freshly prepared as described below, the depth of the layer being 40 mm. The Standard color solutions listed in the U.S. Pharmacopeia 2012 (USP Monograph 631, Color and Achromicity) or in the European Pharmacopoeia 5.0 (EP Method 2.2.2, Degree of Coloration of Liquids) can be used for confirmation of the appropriate color assignment.

The term "1,4-dihydroxy-2-naphthoate (DHNA)" is a chemical product derived from $E.\ coli$ cells. Okada Y, Tsuzuki Y, Miyazaki J, Matsuzaki K, Hokari R, Komoto S, et al. (2006) Gut 55: 681-8. DHNA is an intermediate in the menaquinone (MK), also known as vitamin K2, biosynthesis pathway of $E.\ coli$ cells. Neidhardt, F. C. (2010) *Escherichia coli* and *Salmonella* (online version: Module 3.2.2 pgs. 36-37); Inledew, W. J. & R. K. Poole (1984) The respiratory chains of *Escherichia coli*. Microbiological reviews. 48: 222-271; Nowicka, B. & J. Cruk (2010) Occurrence, Biosynthesis and Function of Isoprenoid Quinones. Biochimica et Biophysica Acta 1797: 1587-1605.

The term "dissolved oxygen" ($dO_2$) is a relative measure of the amount of oxygen that is dissolved or carried in a given medium. It can be measured with a dissolved oxygen probe such as an oxygen sensor in liquid media.

The term "ferment" or "fermenting" as used herein means the process of culturing prokaryotic host cells that have been transformed to induce the production of a recombinant protein of interest.

The term "filtered bulk" or "filtered bulk substance (FBS)" means the recombinant protein of interest product after harvest and purification, wherein the protein has been released from the host cell, centrifuged and/or filtered to remove any cell debris, purified over suitable chromatography columns, and subsequently concentrated by a filtration process.

The term "harvested cell culture fluid", also denoted as HCCF, means prokaryotic or eukaryotic cell culture fluid from which the cells have been removed, by means including centrifugation or filtration. Cell culture is the process by which either prokaryotic or eukaryotic cells are grown under controlled conditions. The term "cell culture" refers to the culturing of cells derived from multicellular eukaryotes, including animal cells or monocellular prokaryotes, including bacteria and yeast. Eukaryotic cell cultures include mammalian cells such as Chinese Hamster Ovary cells, hybridomas, and insect cells. With an appropriate cell culture vessel, secreted proteins can be obtained from anchorage dependent cells or suspension cell lines. Mammalian cell cultures include Chinese Hamster Ovary (CHO) cells or NS0 cells.

The term "harvest operations" or "harvesting" means, without limitation, a process comprising the lysing or homogenization, and then centrifugation and/or filtration of a fermented prokaryotic host cell culture that has been transformed to produce a recombinant protein of interest, in order to begin isolating and purifying said protein of interest.

The term "Hi-dO" as used herein refers to an enhanced process as described herein which is the maintenance of a dissolved oxygen level greater than 0% during harvest operations. To achieve this, the present invention contemplates a combination of overlay air, backpressure and agitation rate that can be used to maintain the $dO_2$ level at or above a set-point, i.e., above 0%, or at about 30% to about 75%, or at levels greater than 75%, or at about 50%, or at levels greater than 50%. In another embodiment, those skilled in the art could also sparge air or pure oxygen into the broth directly to achieve Hi-dO of dissolved oxygen levels greater than 0%.

The term "homogenization" as used herein means a process of lysing or the mechanical cell lysis of prokaryotic host cells transformed with a recombinant protein of interest in order to release said protein from the host cell.

The term "increased back-pressure" is used to increase the oxygen transfer rate through the culture broth. Back-pressure is typically measured either in psi or bar.

"Menaquinones (MK)" are vitamin $K_2$ homologs and serve as electron shuttle molecules in the respiratory chain between membrane bound protein complexes during microaerobic and/or anaerobic conditions. The term "menE" is a gene in the biosynthesis pathway to make menaquinones.

The term "microbial fermentation" means cell culture of bacteria or yeast which is genetically engineered to produce proteins and small molecules (e.g. secondary metabolites). Fermentation is used to propagate recombinant bacteria and yeast as well as other microorganisms and produce proteins of value. The cell productivity and growth of these organisms are maximized by supplying particular growth media and controlling and various environmental factors (such as pH, temperature, and aeration). Bacterial fermentation fluid may be derived from *E. coli* cultures.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al (1975) Nature 256:495, or may be made by recombinant DNA methods (U.S. Pat. No. 4,816,567). The "monoclonal antibodies" may also be isolated from phage antibody libraries using the techniques described for example in Clackson et al (1991) Nature, 352:624-628; Marks et al (1991) J. Mol. Biol., 222:581-597.

The term "overlay air" means air blown in from the top of the fermentor which contains the culture broth. Typically, oxygen is supplied to a fermentor by bubbling air through the liquid culture medium, often accompanied by vigorous agitation to effect a fine bubble dispersion.

The term "prokaryotic host cell" as used in the present invention should encompass those that utilize the menaquinone biosynthesis pathway. In one embodiment, prokaryotic host cells encompass, for example, *Archaebacteria* and *Eubacteria*, such as gram-negative or gram-positive organisms. Examples of useful bacteria include *Escherichia* (e.g., *E. coli*), *Bacilli* (e.g., *B. subtilis*), *Enterobacteria*, *Pseudomonas* species (e.g., *P. aeruginosa*), *Salmonella typhimurium, Serratia marcescans, Klebsiella, Proteus, Shigella, Rhizobia, Vitreoscilla,* or *Paracoccus*. In one embodiment, gram-negative cells are used. In another embodiment, *E. coli* cells are used as hosts for the invention (Bachmann, Cellular and Molecular Biology, vol. 2 (Washington, D.C.: American Society for Microbiology, 1987), pp. 1190-1219; ATCC Deposit No. 27,325) and derivatives thereof, including strain 33D3 having genotype W3110 ΔfhuA (ΔtonA) ptr3 lacIq lacL8 ΔompT Δ(nmpC-fepE) degP41 kan$^R$ (U.S. Pat. No. 5,639,635). Of course other strains and derivatives thereof, such as *E. coli* 294 (ATCC 31,446), *E. coli* B, *E. coli*), 1776 (ATCC 31,537) and *E. coli* RV308 (ATCC 31,608) are also suitable. These examples are illustrative rather than limiting. Methods for constructing derivatives of any of the above-mentioned bacteria having defined genotypes are known in the art and described in, for example, Bass et al. (1990) Proteins, 8: 309-314. It is, of course, necessary to select the appropriate bacteria taking into consideration replicability of the replicon in the cells of a bacterium. For example, *E. coli, Serratia,* or *Salmonella* species can be suitably used as the host when well known plasmids such as pBR322, pBR325, pACYC177, or pKN410 are used to supply the replicon.

As used herein, "recombinant protein" refers generally to peptides and proteins, including antibodies. Such recombinant proteins are "heterologous," i.e., foreign to the host cell being utilized, such as a human protein produced by *E. coli*. The polypeptide may be produced as an insoluble aggregate or as a soluble polypeptide in the periplasmic space or cytoplasm.

The term "scale-independent" means the volume capacity of the fermentation process of the present invention can be accomplished using any scale, such as, for example, from about 1 liter or greater, or about 10 liters or greater, or about 100 liters or greater, or about 500 liters or greater, or about 1,000 liters or greater, or about 10,000 liters or greater, or about 100,000 liters or greater.

II. Modes for Carrying Out the Invention

The present invention concerns improved methods of recombinant production of proteins in a prokaryotic system. The invention is based on preventing a brown adduct formation discovered during the manufacturing of a recombinant protein which caused certain lots of the product to not meet specifications. As illustrated in the examples provided herein, the problem of the brown adduct resulted from an inconsistent redox potential during the harvest operations. It has now been surprisingly discovered that the brown adduct formation can be prevented by maintaining a dissolved oxygen environment greater than zero during the harvest operations or alternatively, by genetically deleting the menE gene in the prokaryotic host cell genome used to recombinantly produce the recombinant protein of interest.

Recombinant Production of Recombinant Proteins in Prokaryotic Cells

In the first step of the above processes, the heterologous nucleic acid (e.g., cDNA or genomic DNA) used to produce the recombinant protein of interest, is suitably inserted into a replicable vector for expression in the bacterium under the control of a suitable promoter for bacteria. Many vectors are available for this purpose, and selection of the appropriate vector will depend mainly on the size of the nucleic acid to be inserted into the vector and the particular host cell to be transformed with the vector. Each vector contains various components depending on its function (amplification of DNA or expression of DNA) and the particular host cell with which it is compatible. The vector components for bacterial transformation may include a signal sequence for the heterologous polypeptide and will include a signal sequence and will also include an inducible promoter for the heterologous polypeptide. They also generally include an origin of replication and one or more marker genes, described herein.

If the heterologous polypeptide is to be secreted, the DNA encoding the heterologous polypeptide of interest herein contains a signal sequence, such as one at the N-terminus of the mature heterologous polypeptide. In general, the signal sequence may be a component of the vector, or it may be a part of the heterologous polypeptide DNA that is inserted into the vector. The heterologous signal sequence selected should be one that is recognized and processed (i.e., cleaved by a signal peptidase) by the host cell. For bacterial host cells that do not recognize and process the native heterologous polypeptide signal sequence, the signal sequence is substituted by any commonly known bacterial signal sequence.

Expression vectors contain a nucleic acid sequence that enables the vector to replicate in one or more selected host cells. Such sequences are well known for a variety of bacteria. The origin of replication from the plasmid pBR322 is suitable for most gram-negative bacteria.

Expression vectors also generally contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli. One example of a selection scheme utilizes a drug to arrest growth of a host cell. Those cells that are successfully transformed with a heterologous gene produce a protein conferring drug resistance and thus survive the selection regimen.

The expression vector for producing a heterologous polypeptide also contains an inducible promoter that is recognized by the host bacterial organism and is operably linked to the nucleic acid encoding the heterologous polypeptide of interest. It also contains a separate inducible or low-basal-expression promoter operably linked to the nucleic acid encoding the lytic enzymes. Inducible promoters suitable for use with bacterial hosts include the .beta.-lactamase and lactose promoter systems (Chang et al., Nature, 275: 615 (1978); Goeddel et al., Nature, 281: 544 (1979)), the arabinose promoter system, including the araBAD promoter (Guzman et al., J. Bacteriol., 174: 7716-7728 (1992); Guzman et al., J. Bacteriol., 177: 4121-4130 (1995); Siegele and Hu, Proc. Natl. Acad. Sci. USA, 94: 8168-8172 (1997)), the rhamnose promoter (Haldimann et al., J. Bacteriol., 180: 1277-1286 (1998)), the alkaline phosphatase promoter, a tryptophan (trp) promoter system (Goeddel, Nucleic Acids Res., 8: 4057 (1980) and EP 36,776), the P.sub.LtetO-1 and P.sub.lac/are-1 promoters (Lutz and Bujard, Nucleic Acids Res., 25: 1203-1210 (1997)), and hybrid promoters such as the tac promoter. deBoer et al., Proc. Nati. Acad. Sci. USA, 80: 21-25 (1983). However, other known bacterial inducible promoters and low-basal-expression promoters are suitable. Their nucleotide sequences have been published, thereby enabling a skilled worker operably to ligate them to DNA encoding the heterologous polypeptide of interest or to the nucleic acids encoding the lytic enzymes (Siebenlist et al., Cell, 20: 269 (1980)) using linkers or adaptors to supply any required restriction sites. If a strong and highly leaky promoter, such as the trp promoter, is used, it is generally used only for expression of the nucleic acid encoding the heterologous polypeptide and not for lytic-enzyme-encoding nucleic acid. The tac and $P_L$ promoters could be used for either, but not both. In one embodiment, the alkaline phosphatase (phoA) promoter is used for the product and the arabinose (ara) promoter for the lytic enzymes.

Promoters for use in bacterial systems also generally contain a Shine-Dalgarno (SD) sequence operably linked to the DNA encoding the heterologous polypeptide of interest. The promoter can be removed from the bacterial source DNA by restriction enzyme digestion and inserted into the vector containing the desired DNA. The phoA promoter can be removed from the bacterial-source DNA by restriction enzyme digestion and inserted into the vector containing the desired DNA.

Construction of suitable vectors containing one or more of the above-listed components employs standard ligation techniques commonly known to those of skill in the art. Isolated plasmids or DNA fragments are cleaved, tailored, and re-ligated in the form desired to generate the plasmids required.

Suitable prokaryotic host cells for the claimed invention include any which utilize the biosynthesis pathway to make menaquinones, as defined herein. Some non-limiting examples may include, for example, *Escherichia coli* (*E. coli*), *Enterobacter, Azotobacter, Erwinia, Bacillus, Pseudomonas, Klebsiella, Proteus, Salmonella, Serratia, Shigella, Rhizobia, Vitreoscilla,* and *Paracoccus.*

Transformation means introducing DNA into the prokaryotic host so that the DNA is replicable, either as an extra-chromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the polypeptides of the invention are grown in media known in the art and suitable for culture of the selected host cells. Examples of suitable media include Luria-Bertani (LB) broth plus necessary nutrient supplements. In certain embodiments, the media also contains a selection agent, chosen based on the construction of the expression vector, to selectively permit growth of prokaryotic cells containing the expression vector. For example, ampicillin is added to media for growth of cells expressing ampicillin resistant gene. Any necessary supplements besides carbon, nitrogen, and inorganic phosphate sources may also be included at appropriate concentrations introduced alone or as a mixture with another supplement or medium such as a complex nitrogen source.

For accumulation of an expressed gene product, the host cell is cultured under conditions sufficient for accumulation of the gene product. Such conditions include, e.g., temperature, nutrient, and cell-density conditions that permit protein expression and accumulation by the cell. Moreover, such conditions are those under which the cell can perform basic cellular functions of transcription, translation, and passage of proteins from one cellular compartment to another for the secreted proteins, as are known to those skilled in the art.

The prokaryotic host cells are cultured at suitable temperatures. For *E. coli* growth, for example, the typical temperature ranges from about 20° C. to about 39° C. In one embodiment, the temperature is from about 25° C. to about 37° C. In another embodiment, the temperature is at about 30° C.

The pH of the culture medium may be any pH from about 5-9, depending mainly on the host organism. For *E. coli*, the pH is from about 6.8 to about 7.4, or about 7.0.

For induction, typically the cells are cultured until a certain optical density is achieved, e.g., an $A_{550}$ of about 80-100, at which point induction is initiated (e.g., by addition of an inducer, by depletion of a repressor, suppressor, or medium component, etc.) to induce expression of the gene encoding the heterologous polypeptide.

After product accumulation, optionally before product recovery, the broth lysate is incubated for a period of time sufficient to release the heterologous polypeptide contained in the cells. In an alternative embodiment, or subsequent to the preceding, the cells present in culture may be lysed mechanically, using any mechanical means known in the art, which may include, for example, chemical lysis or osmotic shock in order to release said protein from the host cell.

Once lysed, the lysate or homogenate may be transferred to a hold tank where it can await the addition of more batches of lysate/homogenate and/or where further processing may occur, such as, for example, dilution with water, addition of buffers or flocculants, pH adjustment, or altering or maintaining the temperature of the lysate/homogenate in preparation for subsequent recovery steps.

In a subsequent step, the heterologous polypeptide, as a soluble or insoluble product released from the cellular matrix, is recovered from the lysate, or homogenate, in a manner that minimizes co-recovery of cellular debris with the product. The recovery may be done by any means, but in one embodiment, can comprise sedimenting refractile particles containing the heterologous polypeptide or collecting supernatant containing soluble product. An example of sedimentation is centrifugation. In this case, the recovery takes place, before expanded bed adsorption (EBA) or sedimentation, in the presence of an agent that disrupts the outer cell wall to increase permeability and allows more solids to be recovered. Examples of such agents include a chelating agent such as ethylenediaminetetraacetic acid (EDTA) or a zwitterion such as, for example, a dipolar ionic detergent such as ZWITTERGENT 316™ detergent. In one embodiment, the recovery takes place in the presence of EDTA.

If centrifugation is used for recovery, the relative centrifugal force (RCF) is an important factor. The RCF is adjusted to minimize co-sedimentation of cellular debris with the refractile particles released from the cell wall at lysis. The specific RCF used for this purpose will vary with, for example, the type of product to be recovered, but is at least about 3000×g, more preferably about 3500-6000×g, or about 4000-6000×g.

The duration of centrifugation will depend on several factors. The sedimentation rate will depend upon, e.g., the size, shape, and density of the retractile particle and the density and viscosity of the fluid. The sedimentation time for solids will depend, e.g., on the sedimentation distance and rate. It is reasonable to expect that the continuous disc-stack centrifuges would work well for the recovery of the released heterologous polypeptide aggregates or for the removal of cellular debris at large scale, since these centrifuges can process at high fluid velocities because of their relatively large centrifugal force and the relatively small sedimentation distance.

The heterologous polypeptide captured in the initial recovery step may then be further purified from the contaminating protein. In one embodiment, the aggregated heterologous polypeptide is isolated, followed by a simultaneous solubilization and refolding of the polypeptide, as disclosed in U.S. Pat. No. 5,288,931. Alternatively, the soluble product is recovered by standard techniques as described below.

General chromatographic methods and their use are known to a person skilled in the art. See for example, Chromatography, 5th edition, Part A: Fundamentals and Techniques, Heftmann, E. (ed) Elsevier Science Publishing Company, New York, (1992); Advanced Chromatographic and Electromigration Methods in Biosciences, Deyl, Z. (ed.), Elsevier Science BV, Amsterdam, The Netherlands, (1998); Chromatography Today, Poole, C. F., and Poole, S. K., Elsevier Science Publishing Company, New York, (1991); Scopes, Protein Purification Principles and Practice (1982); Sambrook, J., et al. (ed), Molecular Cloning: A Laboratory Manual, Second Edition, Cold Spring Harbor Laboratory Press, Cold Spring Harbor, N.Y., 1989; or Current Protocols in Molecular Biology, Ausubel, F. M., et al. (eds), John Wiley & Sons, Inc., New York. The following procedures are exemplary of suitable purification procedures for the soluble heterologous polypeptide released from the periplasm or the cytoplasm, and are well known in the art: fractionation on immunoaffinity or ion-exchange columns; ethanol precipitation; reversed-phase HPLC; chromatography on silica or on a cation-exchange resin such as DEAE; chromatofocusing; SDS-PAGE; ammonium sulfate precipitation; and gel filtration using, for example, SEPHADEX™ G-75.

In one aspect of the invention, the antibody production is conducted in large quantity by a fermentation process. Various large-scale fed-batch fermentation procedures are available for production of recombinant proteins. Large-scale fermentations have at least 1000 liters of capacity, preferably about 1,000 to 100,000 liters of capacity. These fermentors use agitator impellers to distribute oxygen and nutrients, especially glucose (the preferred carbon/energy source). Small-scale fermentation refers generally to fermentation in a fermentor that is no more than approximately 20 liters in volumetric capacity.

As discussed herein, the claimed invention can be used to produce recombinant proteins, including, for example, peptides and proteins, including antibodies.

Examples of recombinant peptides and proteins that can be produced by the method of the invention include, but are not limited to, molecules such as, e.g., renin, a growth hormone, including human growth hormone; bovine growth hormone; growth hormone releasing factor; parathyroid hormone; thyroid stimulating hormone; lipoproteins; α1-antitrypsin; insulin A-chain; insulin B-chain; proinsulin; thrombopoietin; follicle stimulating hormone; calcitonin; luteinizing hormone; glucagon; clotting factors such as factor VIIIC, factor IX, tissue factor, and von Willebrands factor; anti-clotting factors such as Protein C; atrial naturietic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; a serum albumin such as human serum albumin; mullerian-inhibiting substance; relaxin A-chain; relaxin B-chain; prorelaxin; mouse gonadotropin-associated peptide; a microbial protein, such as beta-lactamase; DNase; inhibin; activin; vascular endothelial growth factor (VEGF); receptors for hormones or growth factors; integrin; protein A or D; rheumatoid factors; a neurotrophic factor such as brain-derived neurotrophic factor (BDNF), neurotrophin-3, -4, -5, or -6 (NT-3, NT-4, NT-5, or NT-6), or a nerve growth factor such as NGF-β; cardiotrophins (cardiac hypertrophy factor) such as cardiotrophin-1 (CT-1); platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19;

erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-13; anti-HER-2 antibody; superoxide dismutase; T-cell receptors; surface membrane proteins; decay accelerating factor; viral antigen such as, for example, a portion of the AIDS envelope; transport proteins; homing receptors; addressins; regulatory proteins.

Antibodies produced by the claimed invention may be monoclonal antibodies that are homogeneous populations of antibodies to a particular antigenic determinant (e.g., a cancer cell antigen, a viral antigen, a microbial antigen, a protein, a peptide, a carbohydrate, a chemical, nucleic acid, or fragments thereof). A monoclonal antibody (MAb) to a target-of-interest can be prepared by using any technique known in the art which provides for the production of antibody molecules by continuous cell lines in culture. These include, but are not limited to, the hybridoma technique originally described by Köhler and Milstein (1975) Nature 256:495-497), the human B cell hybridoma technique (Kozbor et al (1983) Immunology Today 4:72), and the EBV-hybridoma technique (Cole et al (1985) in Monoclonal Antibodies and Cancer Therapy, Alan R. Liss, Inc., pp. 77-96). Such antibodies may be of any immunoglobulin class including IgG, IgM, IgE, IgA, and IgD and any subclass thereof. The hybridoma producing the MAbs of use in this invention may be cultivated in vitro or in vivo.

Useful monoclonal antibodies include, but are not limited to, human monoclonal antibodies, humanized monoclonal antibodies, antibody fragments, or chimeric human-mouse (or other species) monoclonal antibodies. Human monoclonal antibodies may be made by any of numerous techniques known in the art (Teng et al (1983) Proc. Natl. Acad. Sci. U.S.A. 80:7308-7312; Kozbor et al (1983) Immunology Today 4:72-79; and Olsson et al (1982) Methods in Enzymology 92:3-16).

The antibody can also be a bispecific antibody. Bispecific antibodies may have a hybrid immunoglobulin heavy chain with a first binding specificity in one arm, and a hybrid immunoglobulin heavy chain-light chain pair (providing a second binding specificity) in the other arm. This asymmetric structure facilitates the separation of the desired bispecific compound from unwanted immunoglobulin chain combinations, as the presence of an immunoglobulin light chain in only one half of the bispecific molecule provides for a facile way of separation (WO 94/04690; Suresh et al (1986) Methods in Enzymology, 121:210; Rodrigues et al (1993) J. of Immunology 151:6954-6961; Carter et al (1992) Bio/Technology 10:163-167; Carter et al (1995) J. of Hematotherapy 4:463-470; Merchant et al (1998) Nature Biotechnology 16:677-681. Methods for making bispecific antibodies are known in the art (Milstein et al (1983) Nature 305:537-539; WO 93/08829; Traunecker et al (1991) EMBO J. 10:3655-3659. Using such techniques, bispecific antibodies can be prepared for conjugation as an antibody drug conjugate (ADC) in the treatment or prevention of disease as defined herein.

The antibody, as defined, can be a functionally active fragment, derivative or analog of an antibody that immunospecifically binds to cancer cell antigens, viral antigens, or microbial antigens or other antibodies bound to tumor cells or matrix. In this regard, "functionally active" means that the fragment, derivative or analog is able to elicit anti-anti-idiotype antibodies that recognize the same antigen that the antibody from which the fragment, derivative or analog is derived recognized. Specifically, in an exemplary embodiment the antigenicity of the idiotype of the immunoglobulin molecule can be enhanced by deletion of framework and CDR sequences that are C-terminal to the CDR sequence that specifically recognizes the antigen. To determine which CDR sequences bind the antigen, synthetic peptides containing the CDR sequences can be used in binding assays with the antigen by any binding assay method known in the art, e.g. the BIA core assay (Kabat et al, (1991) in Sequences of Proteins of Immunological Interest, Fifth Edition, National Institute of Health, Bethesda, Md.; Kabat et al (1980) J. of Immunology 125(3):961-969).

Other useful antibodies include fragments of antibodies such as, but not limited to, F(ab')2 fragments, which contain the variable region, the light chain constant region and the CH1 domain of the heavy chain can be produced by pepsin digestion of the antibody molecule, and Fab fragments, which can be generated by reducing the disulfide bridges of the F(ab')2 fragments. Other useful antibodies are heavy chain and light chain dimers of antibodies, or any minimal fragment thereof such as Fvs or single chain antibodies (SCAs) (e.g., as described in U.S. Pat. No. 4,946,778; Bird (1988) Science 242:423-42; Huston et al., (1988) Proc. Natl. Acad. Sci. U.S.A. 85:5879-5883; and Ward et al (1989) Nature 334:544-54), or any other molecule with the same specificity as the antibody.

The antibody may be a fusion protein of an antibody, or a functionally active fragment thereof, for example in which the antibody is fused via a covalent bond (e.g., a peptide bond), at either the N-terminus or the C-terminus to an amino acid sequence of another protein (or portion thereof, such as at least 10, 20 or 50 amino acid portion of the protein) that is not the antibody. The antibody or fragment thereof may be covalently linked to the other protein at the N-terminus of the constant domain.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al (1984) Proc. Natl. Acad. Sci. U.S.A., 81:6851-6855). A chimeric antibody is a molecule in which different portions are derived from different animal species, such as those having a variable region derived from murine monoclonal and human immunoglobulin constant regions (U.S. Pat. Nos. 4,816,567; 4,816,397). Chimeric antibodies include "primatized" antibodies comprising variable domain antigen-binding sequences derived from a non-human primate (e.g., Old World Monkey, Ape etc) and human constant region sequences.

Chimeric and humanized monoclonal antibodies, comprising both human and non-human portions, can be made using standard recombinant DNA techniques (WO 87/02671; EP 184,187; EP 171496; EP 173494; WO 86/01533; U.S. Pat. No. 4,816,567; EP 12023; Berter et al (1988) Science 240: 1041-1043; Liu et al (1987) Proc. Natl. Acad. Sci. U.S.A. 84: 3439-3443; Liu et al (1987) J. Immunol. 139: 3521-3526; Sun et al (1987) Proc. Natl. Acad. Sci. U.S.A. 84: 214-218; Nishimura et al (1987) Cancer. Res. 47: 999-1005; Wood et al (1985) Nature 314: 446-449; and Shaw et al (1988) J. Natl. Cancer Inst. 80: 1553-1559; Morrison (1985) Science 229: 1202-1207; Oi et al (1986) BioTechniques 4: 214; U.S. Pat. No. 5,225,539;

Jones et al (1986) Nature 321:552-525; Verhoeyan et al (1988) Science 239: 1534; and Beidler et al (1988) J. Immunol. 141: 4053-4060; each of which is incorporated herein by reference in its entirety.

Therapeutic monoclonal antibodies that may be produced by the methods of the invention include, for are not limited to, trastuzumab (HERCEPTIN®, Genentech, Inc., Carter et al (1992) Proc. Natl. Acad. Sci. U.S.A., 89:4285-4289; U.S. Pat. No. 5,725,856); anti-CD20 antibodies such as chimeric anti-CD20 "C2B8" (U.S. Pat. No. 5,736,137); rituximab (RITUXAN®), ocrelizumab, a chimeric or humanized variant of the 2H7 antibody (U.S. Pat. No. 5,721,108; WO 04/056312) or tositumomab (BEXXAR®); anti-IL-8 (St John et al (1993) Chest, 103:932, and WO 95/23865); antibodies targeting other interleukins, such as IL-1, IL-2, IL-3, IL-4, IL-5, IL-6, IL-7, IL-9, IL-10, IL-12, IL-13; anti-VEGF antibodies including humanized and/or affinity matured anti-VEGF antibodies such as the humanized anti-VEGF antibody huA4.6.1 bevacizumab (AVASTIN®, Genentech, Inc., Kim et al (1992) Growth Factors 7: 53-64, WO 96/30046, WO 98/45331); anti-PSCA antibodies (WO 01/40309); anti-CD40 antibodies, including S2C6 and humanized variants thereof (WO 00/75348); anti-CD11a (U.S. Pat. No. 5,622,700; WO 98/23761; Steppe et al (1991) Transplant Intl. 4:3-7; Hourmant et al (1994) Transplantation 58:377-380); anti-IgE (Presta et al (1993) J. Immunol. 151:2623-2632; WO 95/19181); anti-CD18 (U.S. Pat. No. 5,622,700; WO 97/26912); anti-IgE, including E25, E26 and E27 (U.S. Pat. Nos. 5,714,338; 5,091,313; WO 93/04173; U.S. Pat. No. 5,714,338); anti-Apo-2 receptor antibody (WO 98/51793); anti-TNF-alpha antibodies including cA2 (REMICADE®), CDP571 and MAK-195 (U.S. Pat. No. 5,672,347; Lorenz et al (1996) J. Immunol. 156(4): 1646-1653; Dhainaut et al (1995) Crit. Care Med. 23(9):1461-1469); anti-Tissue Factor (TF) (EP 0 420 937 B1); anti-human alpha 4 beta 7 integrin (WO 98/06248); anti-EGFR, chimerized or humanized 225 antibody (WO 96/40210); anti-CD3 antibodies such as OKT3 (U.S. Pat. No. 4,515,893); anti-CD25 or anti-tac antibodies such as CHI-621 SIMULECT® and ZENAPAX® (U.S. Pat. No. 5,693,762); anti-CD4 antibodies such as the cM-7412 antibody (Choy et al (1996) Arthritis Rheum 39(1): 52-56); anti-CD52 antibodies such as CAMPATH-1H (Riechmann et al (1988) Nature 332: 323-337); anti-Fc receptor antibodies such as the M22 antibody directed against Fc gamma RI as in Graziano et al (1995) J. Immunol. 155(10): 4996-5002; anti-carcinoembryonic antigen (CEA) antibodies such as hMN-14 (Sharkey et al (1995) Cancer Res. 55(23 Suppl): 5935s-5945s; antibodies directed against breast epithelial cells including huBrE-3, hu-Mc 3 and CHL6 (Ceriani et al (1995) Cancer Res. 55(23): 5852s-5856s; and Richman et al (1995) Cancer Res. 55(23 Supp): 5916s-5920s); antibodies that bind to colon carcinoma cells such as C242 (Litton et al (1996) Eur J. Immunol. 26(1):1-9); anti-CD38 antibodies, e.g. AT 13/5 (Ellis et al (1995) J. Immunol. 155(2): 925-937); anti-CD33 antibodies such as Hu M195 (Jurcic et al (1995) Cancer Res 55(23 Suppl): 5908s-5910s and CMA-676 or CDP771; anti-CD22 antibodies such as LL2 or LymphoCide (Juweid et al (1995) Cancer Res 55(23 Suppl): 5899s-5907s); anti-EpCAM antibodies such as 17-1A (PANOREX®); anti-GpIIb/IIIa antibodies such as abciximab or c7E3 Fab (REOPRO®); anti-RSV antibodies such as MEDI-493 (SYNAGIS®); anti-CMV antibodies such as PROTOVIR®); anti-HIV antibodies such as PRO542; anti-hepatitis antibodies such as the anti-Hep B antibody OSTAVIR®); anti-CA 125 antibody OvaRex; anti-idiotypic GD3 epitope antibody BEC2; anti-human renal cell carcinoma antibody such as ch-G250; ING-1; anti-human 17-1A antibody (3622W94); anti-human colorectal tumor antibody (A33); anti-human melanoma antibody R24 directed against GD3 ganglioside; anti-human squamous-cell carcinoma (SF-25); and anti-human leukocyte antigen (HLA) antibodies such as Smart ID10 and the anti-HLA DR antibody Oncolym (Lym-1).

III. Methods and Assays

Analytical Methods/Assays
Clarity, Opalescence and Coloration (COC) Assay

The degree of opalescence may also be determined by instrumental measurement of the light absorbed or scattered on account of submicroscopic optical density in homogeneities of opalescent solutions and suspensions. Such techniques are nephelometry and turbidimetry. For turbidity measurement of coloured samples, ratio turbidimetry and nephelometry with ratio selection are used. The light scattering effect of suspended particles can be measured by observation of either the transmitted light (turbidimetry) or the scattered light (nephelometry). Ratio turbidimetry combines the principles of both nephelometry and turbidimetry. Turbidimetry and nephelometry are useful for the measurement of slightly opalescent suspensions. Reference suspensions produced under well-defined conditions must be used. Standard color solutions listed in the U.S. Pharmacopeia 2012 (USP Monograph 631, Color and Achromicity) or in the European Pharmacopoeia 5.0 (EP Method 2.2.2, Degree of Coloration of Liquids) for confirmation of the appropriate color assignment. For quantitative measurements the construction of calibration curves is essential, since the relationship between the optical properties of the suspension and the concentration of the dispersed phase is at best semi-empirical. The determination of opalescence of coloured liquids is done with ratio turbidimeters or nephelometers with ratio selection since colour provides a negative interference, attenuating both incident and scattered light and lowering the turbidity value. The effect is so great for even moderately coloured samples that conventional nephelometers cannot be used. The instrumental assessment of clarity and opalescence provides a more discriminatory test that does not depend on the visual acuity of the analyst. Numerical results are more useful for quality monitoring and process control, especially in stability studies. For example, previous numerical data on stability can be projected to determine whether a given batch of dosage formulation or active pharmaceutical ingredient will exceed shelf-life limits prior to the expiry date.

HPLC Assay

High Performance Liquid Chromatography, also known as High Pressure Liquid Chromatography, abbreviated as HPLC, is a special form of liquid chromatography and nowadays used frequently in biochemistry and analytical chemistry. The analyte is forced through a column of the stationary phase in a liquid (mobile phase) at high pressure, which decreases the time the separated components remain on the stationary phase and thus the time they have to diffuse within the column. This leads to narrower peaks in the resulting chromatogram and thence to better resolution and sensitivity as compared to LC. The mobile phase is chosen to ensure solubility of the sample solutes. For the stationary phase, preferably microparticulate silica (bare or chemically modified) is used, because its high surface area accentuates the differences in solute-stationary phase interactions. The use of a stationary phase that interacts strongly with solutes relative to solute mobile-phase interactions will result in very long retention times, a situation which is not analytically useful. Hence the stationary phase must be selected so as to provide weak to moderate solute interactions relative to those in the mobile phase. As a consequence, the nature of the solute governs the type of LC selected. The stronger interactions should occur in the mobile phase to ensure sample solubility and ready elution, while the stationary phase should be responsive to more subtle differences among the solutes. For example, polar neutral compounds are usually better analyzed using a polar mobile phase together with a nonpolar stationary phase that distinguishes subtle differences in the dispersive character of the solutes. One of the powerful aspects of HPLC is that the mobile phase can be varied to alter the retention mechanism. Modifiers can be added to the mobile phase to control retention. For example, pH is an important variable in aqueous mobile phases.

Reversed-phase chromatography (RP-HPLC) calls for the use of a non-polar stationary phase and a polar mobile phase (composed of one or more of the polar solvents, e.g. water, methanol, acetonitrile, and tetrahydrofuran).

Hydrophobic interaction chromatography (HIC) HPLC: This chromatographic method is good for analyzing proteins or antibody/protein bioconjugates based on their hydrophobicity. The theory behind hydrophobic interaction chromatography is that proteins are bound to the resin by employing an aqueous high salt mobile phase. The salt conditions contribute to a lyotropic effect which allows the proteins to bind to the lower surface coverage of a hydrophobic ligand. Proteins are eluted by the simple technique of decreasing the salt concentration. Most therapeutic targets are eluted in a low salt or a no salt buffer. Thus, the compound can be eluted in a more polar and less denaturing environment. For example, HIC has been used extensively to analyze drug loading in antibody-drug or protein-drug conjugates.

NMR Assay

Nuclear magnetic resonance (NMR) detection is based on the fact that certain nuclei with odd-numbered masses, including H and 13C, spin about an axis in, a random fashion. However, when placed between poles of a strong magnet, the spins are aligned either parallel or anti-parallel to the magnetic field, with the parallel orientation favored since it is slightly lower in energy. The nuclei are then irradiated with electromagnetic radiation which is absorbed and places the parallel nuclei into a higher energy state; consequently, they are now in "resonance" with the radiation. Each H or C will produce different spectra depending on their location and adjacent molecules, or elements in the compound, because all nuclei in molecules are surrounded by electron clouds which change the encompassing magnetic field and thereby alter the absorption frequency.

Mass Spectrometry

Mass spectrometry is an analytical technique used to measure the mass-to-charge ratio (m/z or m/q) of ions. It is most generally used to analyze the composition of a physical sample by generating a mass spectrum representing the masses of sample components. The technique has several applications including identifying unknown compounds by the mass of the compound and/or fragments thereof determining the isotopic composition of one or more elements in a compound, determining the structure of compounds by observing the fragmentation of the compound, quantitating the amount of a compound in a sample using carefully designed methods (mass spectrometry is not inherently quantitative), studying the fundamentals of gas phase ion chemistry (the chemistry of ions and neutrals in vacuum), and determining other physical, chemical or even biological properties of compounds with a variety of other approaches.

A mass spectrometer is a device used for mass spectrometry, and it produces a mass spectrum of a sample to analyze its composition. This is normally achieved by ionizing the sample and separating ions of differing masses and recording their relative abundance by measuring intensities of ion flux. A typical mass spectrometer comprises three parts: an ion source, a mass analyzer, and a detector.

The kind of ion source is a contributing factor that strongly influences-what types of samples can be analyzed by mass spectrometry. Electron ionization and chemical ionization are used for gases and vapors. In chemical ionization sources, the analyte is ionized by chemical ion-molecule reactions during collisions in the source. Two techniques often used with liquid and solid biological samples include electrospray ionization (ESI) and matrix-assisted laser desorption/ionization (MALDI). Other techniques include fast atom bombardment (FAB), thermospray, atmospheric pressure chemical ionization (APCI), secondary ion mass spectrometry (SIMS), and thermal ionisation.

UV Spectroscopy

Ultraviolet-visible spectroscopy or ultraviolet-visible spectrophotometry (UV-Vis or UV/Vis) refers to absorption spectroscopy or reflectance spectroscopy in the ultraviolet-visible spectral region. This means it uses light in the visible and adjacent (near-UV and near-infrared (NIR)) ranges. The absorption or reflectance in the visible range directly affects the perceived color of the chemicals involved. In this region of the electromagnetic spectrum, molecules undergo electronic transitions. This technique is complementary to fluorescence spectroscopy, in that fluorescence deals with transitions from the excited state to the ground state, while absorption measures transitions from the ground state to the excited state. A UV spectrometer is an instrument that uses a beam of light from a visible and/or UV light source (colored red) is separated into its component wavelengths by a prism or diffraction grating. Each monochromatic (single wavelength) beam in turn is split into two equal intensity beams by a half-mirrored device. One beam, the sample beam (colored magenta), passes through a small transparent container (cuvette) containing a solution of the compound being studied in a transparent solvent. The other beam, the reference (colored blue), passes through an identical cuvette containing only the solvent. The intensities of these light beams are then measured by electronic detectors and compared. The intensity of the reference beam, which should have suffered little or no light absorption, is defined as JO. The intensity of the sample beam is defined as I. Over a short period of time, the spectrometer automatically scans all the component wavelengths in the manner described. The ultraviolet (UV) region scanned is normally from 200 to 400 nm, and the visible portion is from 400 to 800 nm.

IV. Examples

The following are examples of methods and compositions of the invention. It is understood that various other embodiments may be practiced, given the general description provided above.

Example 1: Adduct Detection

Figure 1:
FIG. 1 shows the COC assay results of three manufacturing runs of a product in which two runs, Run 2 and Run 3, did not meet the expected results for the COC assay. PW=purified water, C=development run control, 1=Run 1, 2=Run 2, and 3=Run 3.

During a manufacture for a particular recombinant protein, seven filtered bulks for storage (FBS) were produced where typical results against product appearance criteria were obtained for five of the seven bulks. Per manufacturing specification, the product specific test instructions require the use of Yellow (Y) color series for the evaluation of the product samples by the COC assay, a method for the determination of clarity/degree of opalescence, degree of coloration, and appearance. However, two bulks (Runs 2 and 3) appeared brown in color and did not meet the expected Yellow series color criterion of ≤Y7 for the COC assay. A comparison of the COC results for Runs 1-3 is shown in FIG. 1. To investigate the discrepancy further, the seven FBS samples were concentrated to increase the intensity of the color. The concentrated samples were compared against all the Standard color solutions listed in the U.S. Pharmacopeia 2012 (USP Monograph 631, Color and Achromicity) or in the European Pharmacopoeia 5.0 (EP Method 2.2.2, Degree of Coloration of Liquids) for confirmation of the appropriate color assignment. The samples were compared in diffused daylight 5 min after preparation of the reference sample, viewing vertically against a black background. The diffusion of light must be such that reference sample I can readily be distinguished from water and that reference suspension II can readily be distinguished from reference suspension I. A liquid was considered clear if its clarity was the same as that of water R or of the solvent used when examined under the conditions described above, or if its opalescence was not more pronounced than that of the reference sample I.

Since the cause of the coloration was unknown for Runs 2 and 3, multiple investigational studies were completed to determine the source and cause of the atypical brown color. Samples from Runs 1-3 were analyzed for metals, trace elements (other than metals), and chromophores. These studies suggested that the coloration observed in Runs 2 and 3 were not due to metals or other trace elements (data not shown).

To determine whether chromophores were associated with the unexpected color observed in the FBS, Runs 1-3 were analyzed using ultraviolet and visible (UV/vis) spectroscopy with a 1 cm path length cuvette. The UV spectra (200-600 nm) did not display any significant differences in the observance profile for the samples analyzed.

Figure 2A:
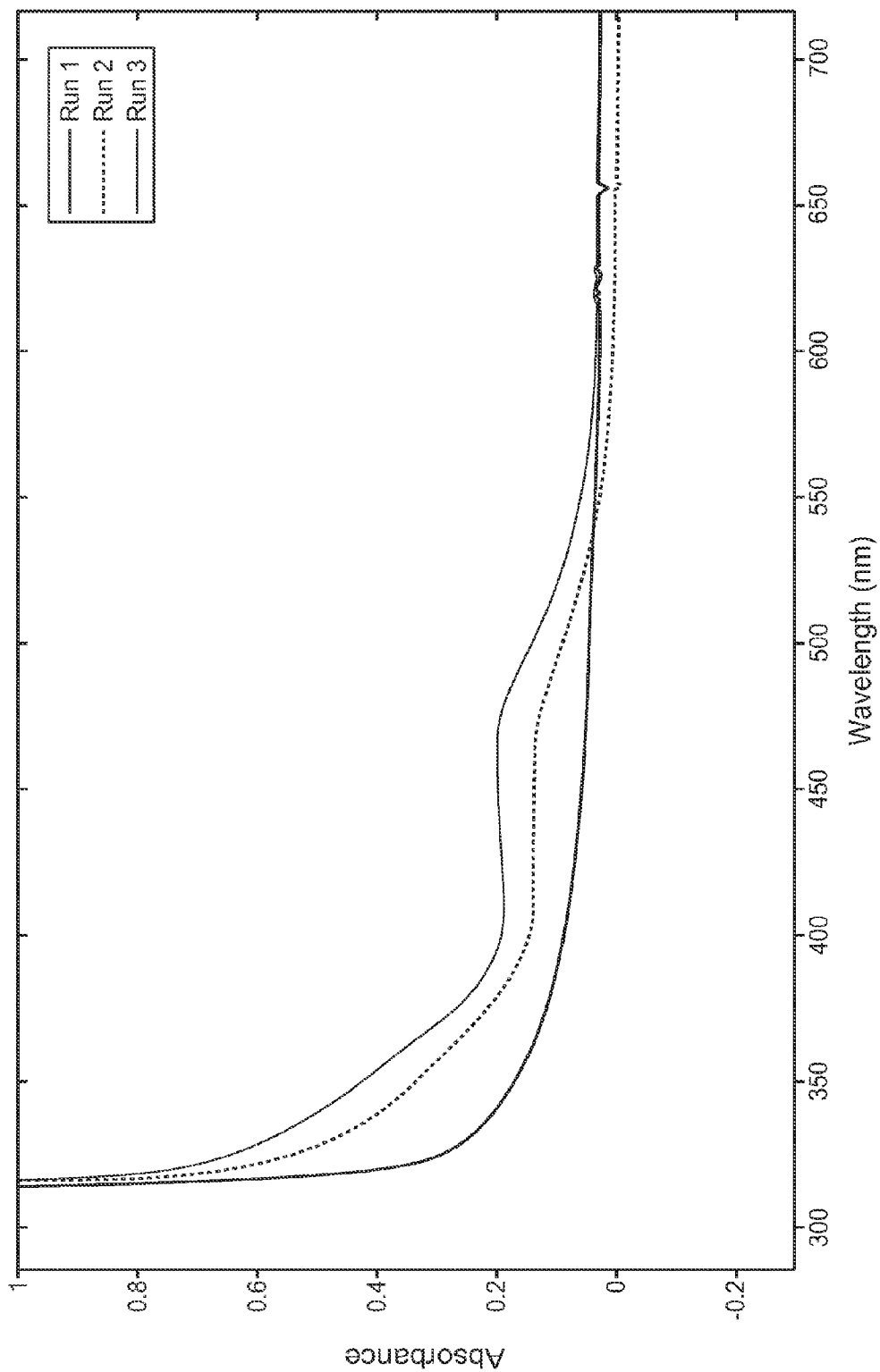
FIG. 2A shows the UV/vis Spectra (10 cm) for Runs 1-3—Near UV, where Runs 1-3 are represented. New absorbance peaks were observed approximately at 320 nm and at 460 nm which were not apparent for Run 1.
Figure 2B:
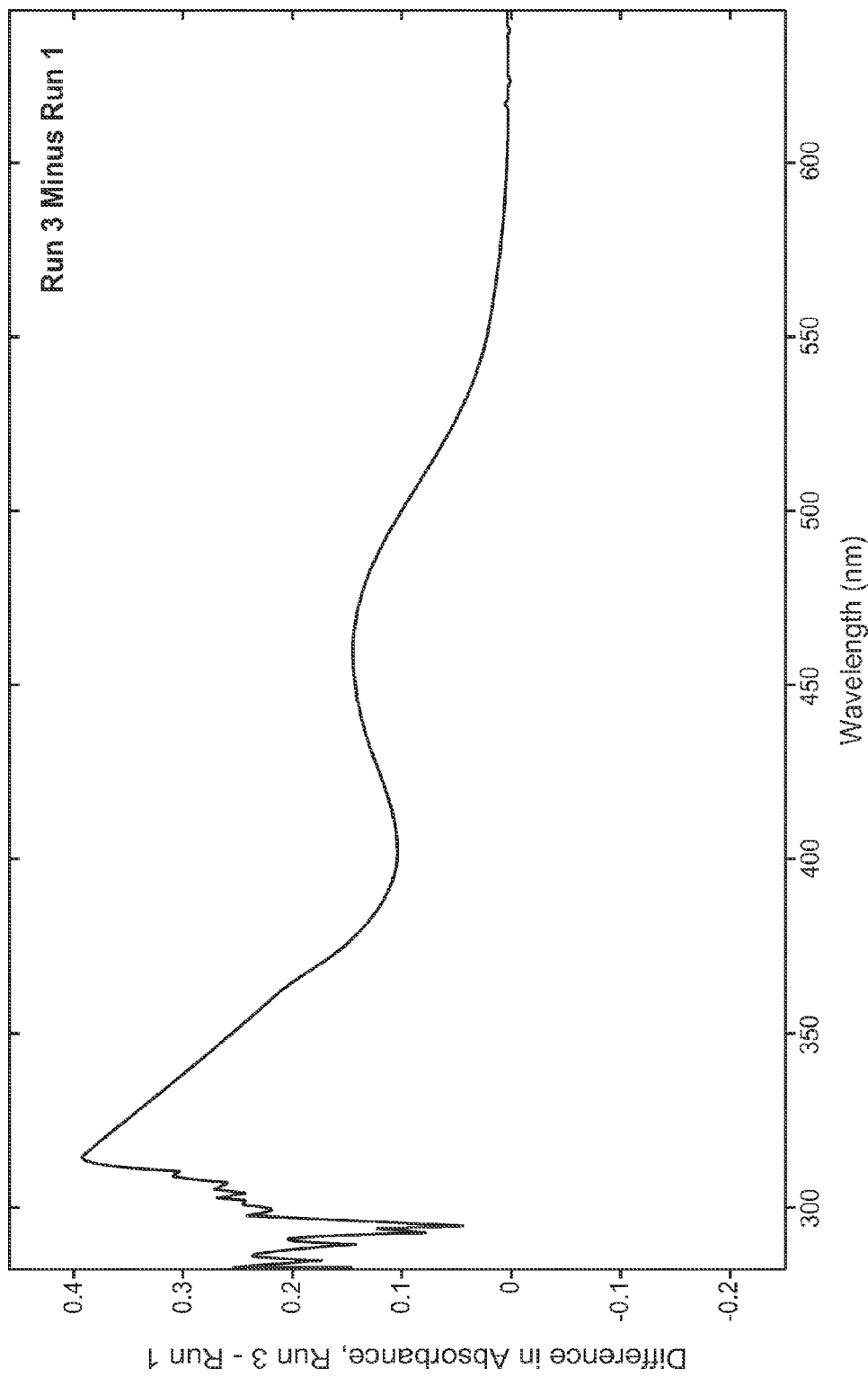
FIG. 2B shows the UV/vis spectra for Run 3 minus Run 1, in which the difference of the absorbance peaks for Runs 2 and 3 can be distinguished from Run 1.

To increase the sensitivity of the UV spectrophotometer, the experiment was repeated using a 10 cm path length cuvette. The 10 cm cuvette offers increased sensitivity to the 1 cm cuvette due to the absorbance of a sample is proportional to the number of absorbing molecules in the spectrophotometer meter light beam. The samples were scanned between 200-700 nm to determine the absorption spectrum of Runs 1-3. The shape of the spectra for Runs 2 and 3 was different than Run 1: new absorbance peaks were observed approximately at 320 nm and at 460 nm which were not apparent for Run 1 (FIG. 2A). This difference can be observed more clearly when the spectrum of Run 1 is subtracted from the spectrum of Run 3 (FIG. 2B). The peak observed at 460 nm for Runs 2 and 3 is consistent with a flavin (e.g., vitamin) fingerprint.

Based on the 10 cm UV/vis results, full spectrum analysis for RP-HPLC and IEC with options for MS detection were performed on FBS from Runs 1-3.

Figure 3:
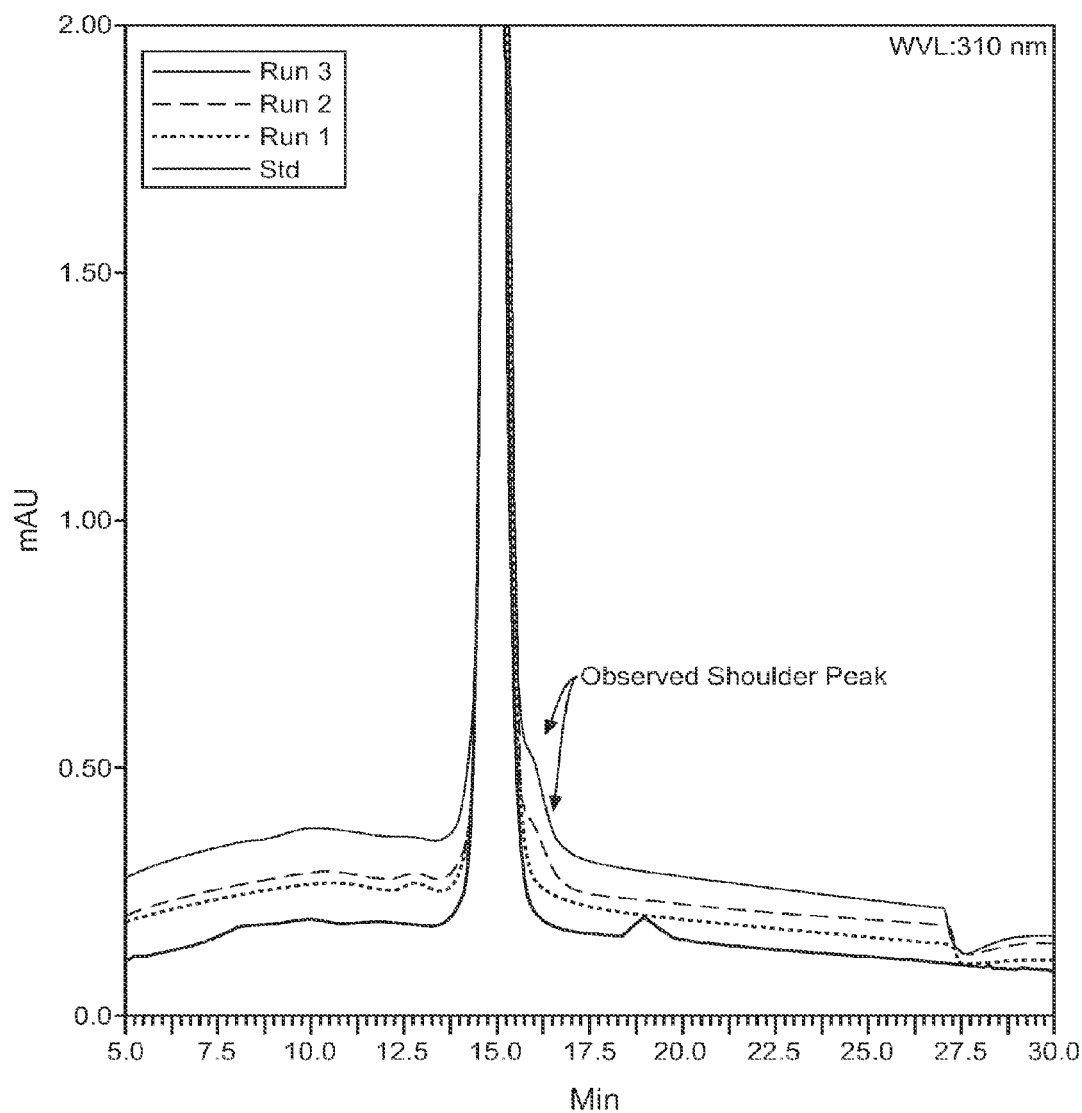
FIG. 3 shows an IEC assay monitored at 310 nm for Runs 1-3. A slight shoulder peak behind the main peak was observed for Runs 2 and 3, while the profile for Run 1 was comparable to the Reference Material.

Using full spectrum detection for RP-HPLC, no chromatographic differences were observed for Run 1-3 (data not shown). However, for IEC at 310 nm, minor differences were observed. As shown in FIG. 3, a slight peak behind the Main Peak is observed for Runs 2 and 3 while the profile for Run 1 is comparable to the Reference Material.

Figure 4:
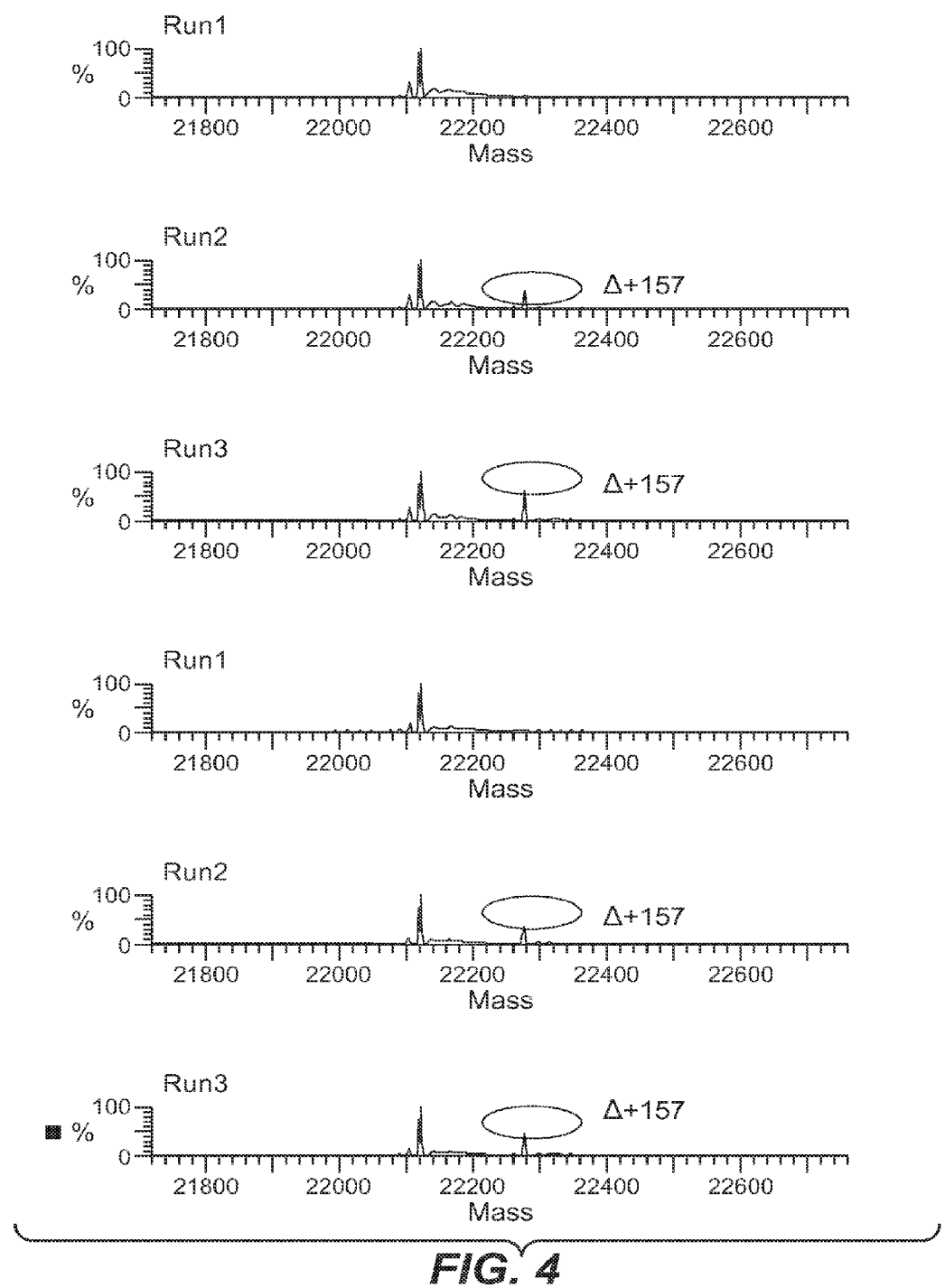
FIG. 4 shows a 2D LC-MS analysis of intact Runs 1-3, monitored at 280 nm and 310 nm. An expected mass was observed for Run 1, while the expected mass and an additional mass at 157 Da were observed for Runs 2 and 3.

Intact samples were submitted for 2D LC-MS and monitored at both 280 and 310 nm. The 2D LC-MS analysis consists of two parts—first dimension is separation by RP-HPLC with the second dimension as fractionated peaks for mass spectrometry analysis. From this experiment, the expected mass was observed for Run 1 while the expected mass and an additional mass of approximately +157 Da were observed for Runs 2 and 3 (FIG. 4).

Example 2: Elucidation of the Adduct

To better elucidate the adduct, Run 3 was selected for fractionation (the minor peak from the IEC assay (FIG. 3) was collected) and further analyzed by 2D-LC MS and mass identification by tryptic peptide map with MS detection.

Figure 5:
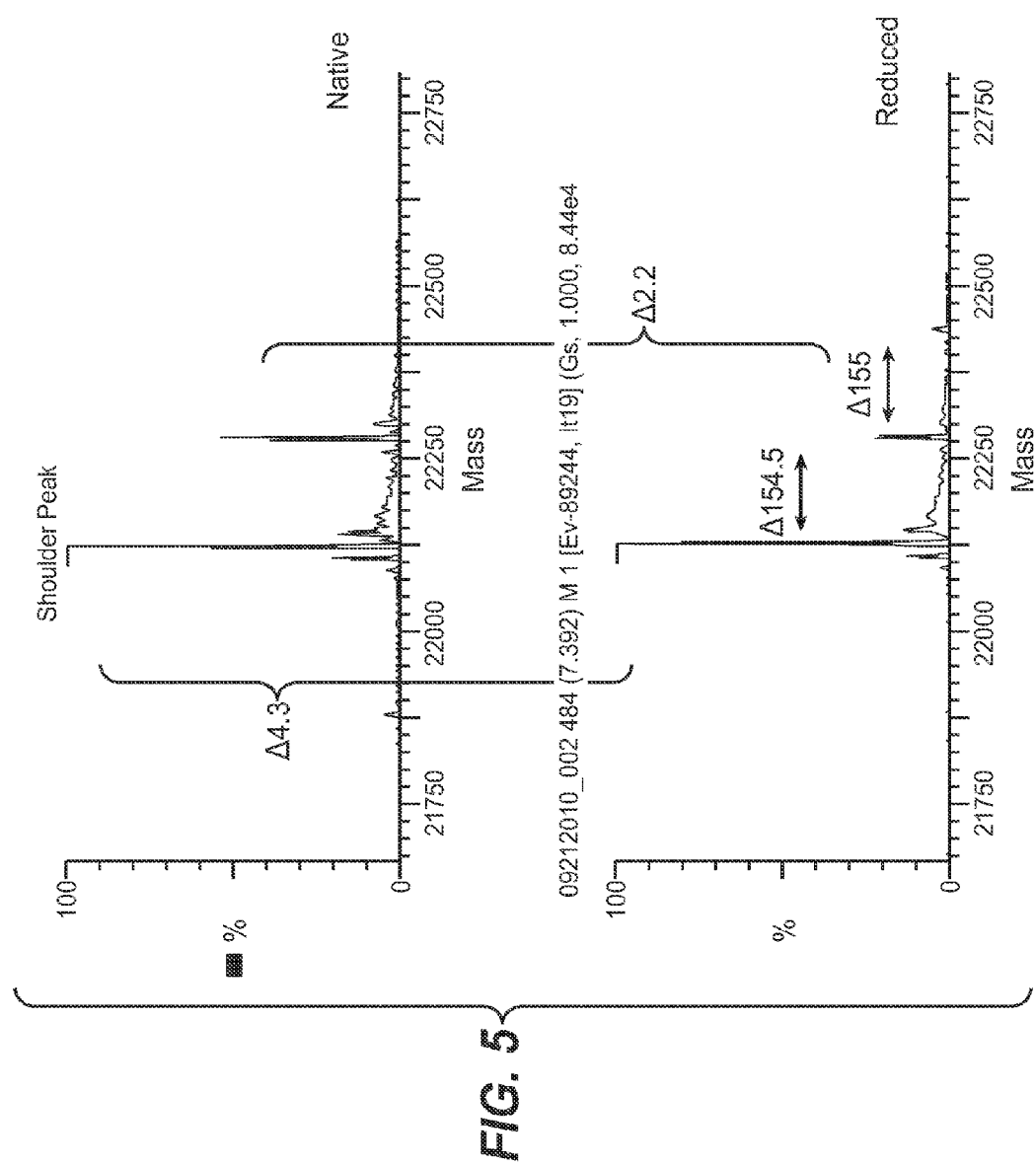
FIG. 5 shows a 2D-LC MS and mass identification by tryptic peptide map with MS detection of a collected fraction of the brown adduct—a minor peak from the IEC assay was collected. From the 2D LC-MS analysis, in addition to the expected mass, a +156 Da mass was observed for the fractionated shoulder peak.

From the 2D LC-MS analysis (FIG. 5), in addition to the expected mass, an approximate +156 Da mass increase was again observed for the fractionated shoulder peak. Upon on-line reduction (with DTT) of the sample, the expected reduced mass was observed. The four additional Daltons observed between the reduced and native analyses are due to the breakage of the disulfide bonds and the addition of four hydrogens. The additional mass was again observed, suggesting the modification was non-reversible or covalent.

Figure 6:
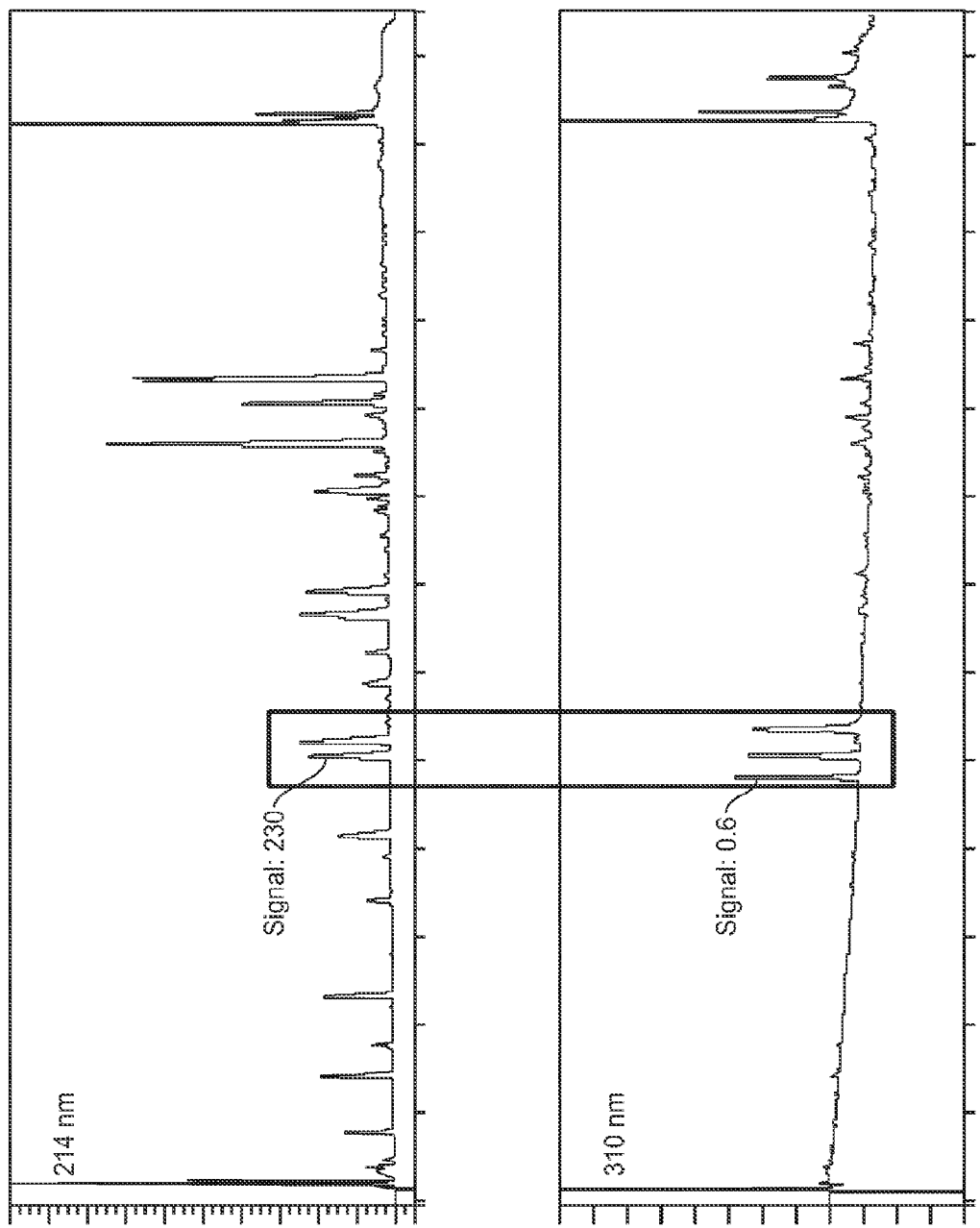
FIG. 6 shows the LC-MS-MS analysis of the novel brown adduct peak observed at 48.8 minutes at 310 nm was determined to be T20 peptide with Cys182 modified with +154.006 Da. Modified (at cysteine, +154.006 Da) and free T6 and T16 peptides were also detected by mass extraction.

From the tryptic peptide map, the sample was collected at both 214 nm and 310 nm. As shown in FIG. 6, novel peaks are enhanced in the 45-55 minute region. LC-MS-MS analysis of the novel peak observed at 48.8 minutes at 310 nm was determined to be T20 peptide with the cysteine residue modified with +154.006 Da. Modified (at cysteine, +154.006 Da) and free T6 and T16 peptides were also detected by mass extraction. Reduced T21 or modified T21 were not detected but this may have been due to the low levels present. The other two peaks observed eluting between 50 to 56 minutes at 310 nm did not contain any unique species when compared to the reference.

1D and 2D 1H NMR analysis was collected to determine the adduct structure. Additional data was acquired using TOSCY (Total Correlation Spectroscopy), HSQC (Heteronuclear Single Quantum Coherence), HMBC (Heteronuclear Multiple Bond Correlation), and ROESY (Rotating-frame Overhauser Effect Spectroscopy (nOe)).

Figure 7:
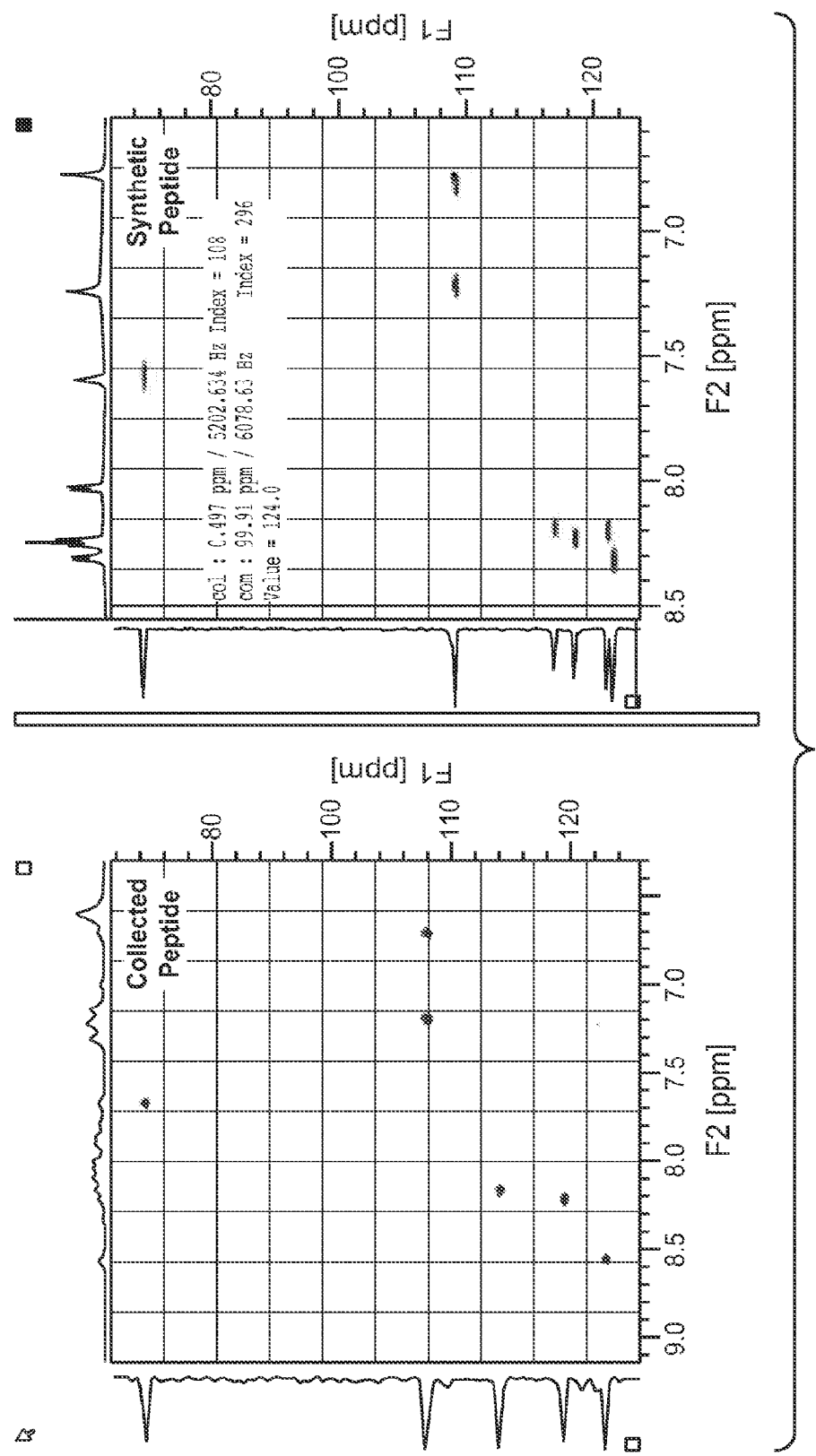
FIG. 7 compares 1H-15N HSQC data of product to a synthetic peptide (NH2-IVQCR-COOH) and showed a Cys NH correlation was missing in the product sample.
Figure 8:
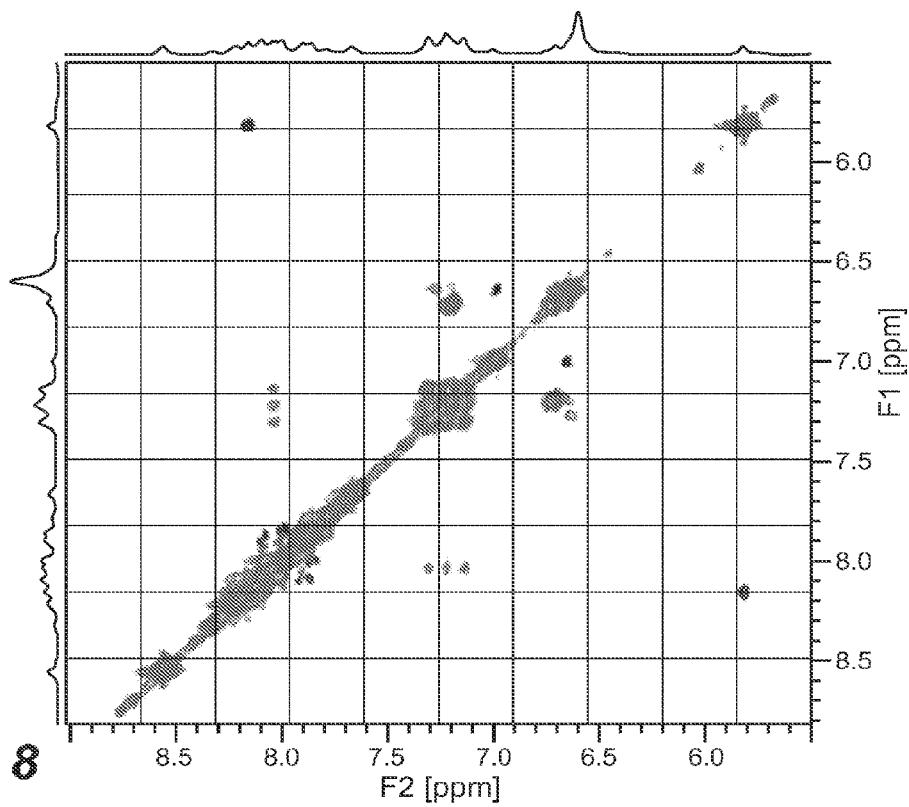
FIG. 8 shows the proposed structure confirmed by strong nOe observed between the CH of Cys and the NH of arginine.

TOCSY creates correlations between all protons that are coupled to each other as well as all other protons within a given spin system. HSQC experiment correlates chemical shifts of directly bound nuclei (i.e. two types of chemical nuclei) while HMBC experiment correlates chemical shifts of two types of nuclei separated from each other with two or more chemical bonds. ROESY utilizes nOe which uses space, not through chemical bonds to confirm a precise molecular conformation (i.e., three dimensional structure of a molecule). The collected peptide observed long range 1H-13C coupling between aromatic (quinone) protons and C=O at 182 ppm. The 1H-13C HSQC chemical shifts for the collected peptide in the aromatic region are a close match to those observed for the synthetic model compound bound to naphthalene-1,4-dione. TOCSY data assigns the Q, V, and R resonances in the product. Comparing 1H-15N HSQC data of product to a synthetic peptide ($NH_2$—IVQCR-COOH) showed a Cys NH correlation was missing in the product sample as shown in FIG. 7. The proposed structure is confirmed by strong nOe observed between the CH of Cys and the NH of Arg (FIG. 8). Based on the NMR data collected, the proposed structure is presented in FIG. 9.

The identification of the colored species as 1,4-dihydroxy-2-naphthoate (DHNA) which formed the recombinant protein-brown adduct was based upon MS, NMR and genetic data. NMR data confirmed that DHNA was attached to the recombinant protein via cysteine residues. DHNA is a product derived from the menaquinone biosynthesis pathway of *E. coli* cells (FIG. 10). Menaquinone is present in *E. coli* but production of it is increased when the culture is in an anaerobic and/or micro-aerobic condition. Menaquinone is used for electron transport in limited oxygen environments and used for returning the disulfide bond forming protein DsbB to the active oxidized state in anaerobic (micro-aerobic) conditions.

Example 3: Hi-dO Process to Mitigate Formation of DHNA-Product Adduct

A control strategy was developed to prevent the generation of a product's free thiols and the subsequent formation of the DHNA-product adduct. The cause of the color formation was determined to be the result of a low redox environment during the harvest operations because Runs 2 and 3 exhibited the highest titers and cell densities, both were subjected to longer hold times for their diluted homogenates, endured longer durations for the homogenates to achieve less than the 15° C. target temperature and had suboptimal homogenate mixing times and rates (data not shown). These factors contributed to generating a low oxygen environment which promoted the reduction of the product disulfide bonds and permitted the opportunity for DHNA to attach to the free thiols of the protein product.

Since the DHNA-protein adduct was formed during the low redox environment during the harvest operations which led to reduced disulfide bonds (i.e. free thiols), an approach was developed to prevent the generation of free thiols and the formation of the DHNA-product adduct. This enhanced process control, called Hi-dO, maintains the dissolved oxygen levels in the harvest operations at greater than zero (>0%) to eliminate the reducing environment (i.e. no free thiol generation).

The formation of the DHNA-product adduct is a complex biological reaction that requires the combination of multiple events across the fermentation and harvest operations. The output of the fermentation process is the production of considerable levels and/or availability of DHNA. The schematic of the three major stages of a typical harvest operation is shown on FIG. 13.

Several process steps were tested post-fermentation/pre-homogenization and tested post-homogenization, to determine if such actions would mitigate the reducing environment or free thiol generation. Such process enhancements tested are shown in Table 1 and FIG. 12.

TABLE 1

Process Enhancements (Hi-dO)

| Post-Fermentation/ Pre-Homogenization | In HMG Hold Tank/ Post-Homogenization |
|---|---|
| Initiate WCB Hi-dO process control: | Dilute homogenate with 2x water prior to homogenate transfer |
| 1. Target $dO_2$ >75% | 1. Temperature control to 10° C. |
| 2. Increase agitation rate (6.3 Watts/L) | 2. Target $dO_2$ >50% by increasing agitation and/or air sparging |
| 3. Apply overlay air (0.6 vvm) | |
| 4. Back-pressure added to about 18.85 psi (1.3 bar) | |
| 5. Process time = 1.5 hours | |
| | Transfer homogenate in water for immediate dilution |
| | Initiate Hi-$dO_2$ homogenate process control: |
| | 6. Maintain Target $dO_2$ >50% |
| | 7. Increase agitation (1-6 Watts/L) |
| | 8. Apply overlay or sparged air (if required) |
| | 9. Process time = 2 hours |

The results of the process enhancements outlined in Table 1 and FIG. 12 are shown in Table 2.

TABLE 2

Product Quality Analyses of Development Runs Performed with the Hi-dO Enhanced Process Controls

| Fermentation Run | IEC % Anomalous Peak @280/310 nm | IEC % Main Peak @280 | RP-HPLC % Peak A | SEC % Monomer | Native SEC % Monomer |
|---|---|---|---|---|---|
| Small-scale (10 L) #1 | 0.00/0.00 | 99.48 | 98.82 | 100.00 | 99.99 |
| Small-scale (10 L) #2 | 0.00/0.00 | 99.69 | 99.00 | 100.00 | 99.97 |
| Manufacturing-scale (1,000 L) | 0.00/0.00 | 99.58 | 99.03 | 100.00 | 99.99 |
| Release Spec FBS CofA | Not defined, but should not be detectable | ≥97% Main Peak | ≥97% Peak A | ≥98% monomer | ≥98% monomer |

A root cause analysis was carried out to understand the origins of the brown coloration. This analysis resulted in the identification of the colored species (DHNA), its attachment to a recombinant protein product, the adduct (DHNA-protein) structure, its origination and the proposed mechanism of how and when DHNA became attached to the product during the production process. As Table 1 summarizes, a mitigation strategy was implemented to prevent formation of the brown adduct, by maintaining the dissolved oxygen level greater than zero (>0%) throughout the harvest operations to eliminate the reducing environment and prevent the formation of product free thiols. As a result, as shown by IEC analyses as the % anomalous peak demonstrated 0%, the brown adduct formation was not detected in the FBS (Table 2).

Example 4: Generating menE Gene-Deleted *E. coli* Host Cells

In addition to the Hi-dO harvest process of the invention, another approach was undertaken to mitigate the brown adduct formation. This involved genetically engineering the prokaryotic host cell such that the menE gene was deleted from the genome, thereby preventing the production of any DHNA intermediate from the menaquinone biosynthesis pathway that could be attached to the recombinant product.

The menE gene deleted host cells were generated as an in-frame, single-gene knockout mutant following the methods described in Baba et al., *Construction of E. coli K-12 in-frame, single-gene knockout mutants: the Keio collection*, Molecular Systems Biology, vol. 21, p. 1-10 (2006) which is hereby incorporated by reference. The menE gene was targeted for mutagenesis with PCR products containing a resistance cassette (such as kanamycin) flanked by FLP recognition target sites and a 50 base pair homologies to the adjacent chromosomal sequences.

The mutagenesis yielded approximately 10-1000 kanamycin resistance colonies when the host cells were incubated aerobically at 37° C. on Luria-Bertani broth (LB) agar containing 30 μg/mL kanamycin.

Example 5: Production of Recombinant Proteins Using menE Gene-Deleted *E. coli* Host Cells The ability of the menE gene-deleted *E. coli* host cells to produce recombinant protein that did not exhibit DHNA-associated protein adduct was tested. Briefly, the menE gene-deleted *E. coli* cells were transformed with plasmid constructs that encoded for two recombinant proteins, PROT 1 and PROT 2, and two recombinant antibodies, AB 1 and AB2, per standard techniques well-known to those of skill in the art (see for example, Simmons et al., Expression of full-length immunoglobulins in *E. coli*: rapid and efficient production of aglycosylated antibodies, J of Immunol Methods 263 p. 133-147 (2002)). Fermentation of the four recombinant proteins/antibodies proceeded as described herein (see also U.S. Pat. No. 6,979,556 which is hereby incorporated by reference).

The filtered bulk recombinant product for all four recombinant protein/antibodies were tested for DHNA-protein adduct formation by IEC assay at 310 nm and showed no detectable DHNA-protein adduct formation (see FIG. 11 for exemplary results for PROT 1).

Surprisingly, it was found that the yield of recombinant product as a result of using the menE deleted *E. coli* cells increased appreciably by about 20% to 50% as compared to the yield using *E. coli* host cells with an intact, wild-type menE gene. Table 3 shows these results.

TABLE 3

Recombinant Protein Yields using menE gene-deleted host cells

| Recombinant Protein | Yield using wild-type *E. coli* host | Yield using menE gene-deleted *E. coli* host | % change |
|---|---|---|---|
| PROT 1 | 1.9 g/L | 2.5 g/L | 30% |
| PROT 2 | 5.5 g/L | 6.5 g/L | 20% |
| AB1 | 0.7 g/L | 1.0 g/L | 40% |
| AB2 | 0.46 g/L | 0.72 g/L | 50% |

What is claimed is:

1. A method of producing a recombinant protein comprising (a) fermenting a menE gene-deleted prokaryotic host cell wherein said prokaryotic host cell has been transformed with a nucleic acid encoding said recombinant protein, (b) harvesting said recombinant protein; and (c) purifying said recombinant protein to a filtered bulk for storage (FBS), wherein said filtered bulk does not contain detectable 1,4-dihydroxy-2-naphthoate (DHNA)-recombinant protein adduct, as measured by an ion exchange chromatography (IEC) assay at 310 nm, and wherein the recombinant protein yield is increased by about 20% or greater, by about 30% or greater, by about 40% or greater, by about 50% or greater, or by about 60% or greater, as compared to the yield using a control prokaryotic host cell.

2. The method of claim 1, wherein the fermentation is scale-independent.

3. The method of claim 1, wherein said recombinant protein is a recombinant polypeptide or an isolated antibody.

4. The method of claim 1, wherein said prokaryotic host cell is *Escherichia coli* (*E. coli*), *Enterobacter*, *Azotobacter*, *Erwinia*, *Bacillus*, *Pseudomonas*, *Klebsiella*, *Proteus*, *Salmonella*, *Serratia*, *Shigella*, *Rhizobia*, *Vitreoscilla*, and *Paracoccus*.

* * * * *